US006867005B2

(12) United States Patent
Keys et al.

(10) Patent No.: US 6,867,005 B2
(45) Date of Patent: Mar. 15, 2005

(54) METHOD AND APPARATUS FOR INCREASING THE DYNAMIC RANGE AND ACCURACY OF BINDING ASSAYS

(75) Inventors: Daniel A. Keys, Irvine, CA (US); Parameswara M. Reddy, Brea, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 104 days.

(21) Appl. No.: 10/032,790

(22) Filed: Oct. 24, 2001

(65) Prior Publication Data

US 2003/0078737 A1 Apr. 24, 2003

(51) Int. Cl.[7] ............................................. G01N 33/53
(52) U.S. Cl. .................. 435/7.1; 435/286.1; 435/287.2; 435/288.7; 436/164; 436/172
(58) Field of Search ................................ 436/164, 172, 436/800, 501; 435/7.1, 973, 286.1, 287.2, 288.7; 422/82.07

(56) References Cited

U.S. PATENT DOCUMENTS

| | | | |
|---|---|---|---|
| 3,791,932 A | 2/1974 | Schuurs et al. | 195/103.5 |
| 4,016,043 A | 4/1977 | Schuurs et al. | 195/103.5 |
| 4,185,084 A | 1/1980 | Mochida et al. | 424/1 |
| 4,243,749 A | 1/1981 | Sadeh et al. | 435/7 |
| 4,313,734 A | 2/1982 | Leuvering | 23/230 |
| 4,373,932 A | 2/1983 | Gribnau et al. | 436/501 |
| 4,401,764 A | 8/1983 | Smith | 436/500 |

(List continued on next page.)

FOREIGN PATENT DOCUMENTS

| | | | |
|---|---|---|---|
| EP | 177191 | 11/1990 | G01N/33/537 |
| GB | 2084317 | 4/1982 | G01N/33/54 |

OTHER PUBLICATIONS

Bass, D.A. et al. "Flow cytometric studies of oxidative product formation by neutrophils: a graded response to membrane stimulation." *J. Immunol.* 130: 1910–1917.
Bode, W. et al. 1989, "Human leukocyte and porcine pancreatic elastase: X–ray crystal structures, mechanism, substrate specificity and mechanism–based inhibitors," *Biochem.* 28:1951–1963.
Coates, P.M. et al., 1975, "A preliminary genetic interpretation of the esterase isozymes of human tissues," *Ann. Hum. Genet. Lond.* 39: 1–20.
Crockard, A. et al., 1982, "Cytochemistry of acid hydrolases in chronic B– and T–cell leukemias," *Am. J. Clin. Pathol.* 78:437–444.
Dujardin, F.H., et al., "Quantitative assessment of cortical bone remodelling from routine radiographs of total hip arthroplasty," *Med. Eng. Phys.* Sep. 1996; 18(6):489–94.
Ferrer–Lopez, P. et al., "Heparin Inhibits Neutrophil–Induced Platelet Activation Via Cathepsin", *J. Lab Clin. Med.* 119(3), 231–239 (1992).
Fleischer, B., 1994, "CD26: a surface protease involved in T–cell activation," *Immunol. Today* 15: 180–184.
Fowler, A., et al., "A multi–modality assay platform for ultra–high throughput screening," *Curr. Pharm. Biotechnol.* Nov. 2000;1(3):265–81.

(List continued on next page.)

*Primary Examiner*—Long V. Le
*Assistant Examiner*—Gary W. Counts
(74) *Attorney, Agent, or Firm*—William H. May; D. David Hill; Liniak, Berenato & White, LLC (57) ABSTRACT

This invention relates to methods for increasing the dynamic range and accuracy of assays in which the presence, absence, activity or concentration of a target analyte is assayed by the emission or quenching of a light signal, or by a change (i.e., an evolution or loss) of a light signal in two or more time intervals. In preferred embodiments multiple digitized images are captured at varying times, and the images analyzed to identify captured images within the dynamic range of the assay. The invention further relates to apparati capable of implementing such methods.

28 Claims, 3 Drawing Sheets

U.S. PATENT DOCUMENTS

| | | | |
|---|---|---|---|
| 4,661,444 A | 4/1987 | Li | 435/7 |
| 4,746,631 A | 5/1988 | Clagett | 436/518 |
| 4,810,096 A | 3/1989 | Russell et al. | 356/436 |
| 4,946,958 A * | 8/1990 | Campbell et al. | 546/104 |
| 5,198,670 A | 3/1993 | VanCauter et al. | 250/328 |
| 5,306,468 A | 4/1994 | Anderson et al. | 422/101 |
| 5,501,985 A | 3/1996 | Baugher et al. | 436/518 |
| 5,563,036 A | 10/1996 | Peterson et al. | 435/6 |
| 5,599,668 A | 2/1997 | Stimpson et al. | 435/6 |
| 5,627,080 A | 5/1997 | Cheng et al. | 436/534 |
| 5,633,141 A | 5/1997 | Lee et al. | 435/7.2 |
| 5,679,525 A | 10/1997 | Peterson et al. | 435/6 |
| 5,691,147 A | 11/1997 | Draetta et al. | 435/7.1 |
| 5,698,411 A | 12/1997 | Lucas et al. | 435/29 |
| 5,747,352 A | 5/1998 | Yan et al. | 436/533 |
| 5,754,229 A | 5/1998 | Elabd | 348/319 |
| 5,772,926 A | 6/1998 | Akhavan-Tafti | 252/700 |
| 5,776,782 A | 7/1998 | Tsuji | 436/171 |
| 5,811,526 A | 9/1998 | Davidson | 530/391.3 |
| 5,843,651 A | 12/1998 | Stimpson et al. | 435/6 |
| 5,851,778 A | 12/1998 | Oh et al. | 435/7.9 |
| 5,876,935 A | 3/1999 | Pankratz et al. | 435/6 |
| 5,939,281 A * | 8/1999 | Lehmann et al. | 435/7.94 |
| 5,965,736 A | 10/1999 | Akhavan-Tafti | 548/110 |
| 5,976,822 A | 11/1999 | Landrum et al. | 435/23 |
| 6,045,727 A | 4/2000 | Akhavan-Tafti et al. | 252/700 |
| 6,045,991 A | 4/2000 | Akhavan-Tafti | 435/4 |
| 6,057,163 A * | 5/2000 | McMillan et al. | 436/172 |
| 6,090,571 A | 7/2000 | Akhavan-Tafti et al. | 435/21 |
| 6,139,782 A | 10/2000 | Akhavan-Tafti et al. | 252/700 |
| 6,177,958 B1 | 1/2001 | Anderson | 348/362 |
| 6,212,291 B1 | 4/2001 | Wang et al. | 382/132 |
| 6,218,137 B1 | 4/2001 | Akhavan-Tafti et al. | 435/21 |
| 6,270,695 B1 | 8/2001 | Akhavan-Tafti et al. | 252/700 |
| 6,287,871 B1 * | 9/2001 | Herron et al. | 436/172 |
| 6,312,960 B1 * | 11/2001 | Balch et al. | 436/518 |
| 6,337,472 B1 * | 1/2002 | Garner et al. | 250/201.3 |
| 6,518,068 B1 | 2/2003 | Gambini et al. | 436/50 |

OTHER PUBLICATIONS

Gartner, T.K. et al., 1985, "The tetrapeptide analogue of the alpha chain and decapeptide analogue of the gamma chain of fibrinogen bind to different sites on the platelet fibrinogen receptor," *Blood* 66 Suppl 1: 305a.

Hegen, M. et al., 1993, "Enzymatic activity of CD26 (dipeptidylpeptidase IV) is not required for its signalling function in T cells," *Immunobiology* 189: 483–493.

Hoffmann, T. et al. 1993, "Dipeptidyl peptidase IV (CD 26) and aminopeptidase N (CD 13) catalyzed hydrolysis of cytokines and peptides with N–terminal cytokine sequences," *FEBS Letters* 336: 61–64.

Hohn, P.A. et al., 1989, "Genomic organization and chromosomal localization of the human cathepsin G gene," *J. Biol. Chem.* 264: 13412–13419.

Houze T.A., et al., "Detection of thymidylate synthase gene expression levels in formalin–fixed paraffin embedded tissue by semiquantitative, nonradioactive reverse transcriptase polymerase chain reaction," *Tumour Biol.* 1997;18(1):53–68.

Jongkind, J.F. et al., 1986, "Detection of acid–b–galactosidase activity in viable human fibroblasts by flow cytometry," *Cytometry* 7:463–466.

Kankaanranta, H. et al., 1994, " Effects of non–steroidal anti–inflammatory drugs on polymorphonuclear leukocyte functions in vitro: focus on fenamates," *Naunyn–Schmiedeberg's Arch Pharmacol.* 350:685–691.

Kohen, E. et al., 1993, "An in situ study of beta–glucosidase activity in normal and gaucher fibroblasts with fluorogenic probes," *Cell Biochem. and Function* 11:167–177.

Kojima, K. et al., 1979, "A new and highly sensitive fluorescence assay for collagenase–like peptidase activity," *Anal. Biochem.* 100:43–50.

Li, C.Y. et al., 1970, "Acid phosphatase isoenzyme in human leukocytes in normal and pathologic conditions," *J. Histochem. Cytochem.* 18:473–481.

Manzella S.M., et al. "A biphasic radiometric assay of glycogenin using the hydrophobic acceptor n–dodecyl–beta–D–maltoside," *Anal. Biochem.* Feb. 1, 1994;216(2):383–91.

McDonald, J.A. et al., 1980, "Degradation of fibronectin by human leukocyte elastase," *J. Biol. Chem.* 255: 8848–8858.

Mentlein, R. et al., H. R., "Influence of Pregnancy on Dipeptidyl Peptidase IV Activity (CD26 Leukocyte Differentiation Antigen) of Circulating Lymphocytes", *Eur. J. Clin. Chem. Clin. Biochem.*, 29, 477–480 (1991).

Messler P., et al., "Instrumentation for multiwavelengths excitation imaging," *J. Neurosci. Methods* Nov. 1996;69(2):137–47).

Rotman, B. et al., 1963, "Fluorogenic substrates for b–D–galactosidases and phosphatases derived from fluorescein (3,6–dihydroxyfluoran) and its monomethyl ether," *Proc. Nat. Acad. Sci. USA* 50:1–6.

Royer, G., et al., "Immobilized Derivatives of Leucine Aminopeptidase and Aminopeptidase M.," *J. Biol. Chem.* 248(5), 1807–1812 (1973).

Ruiz, P. et al., 1996, "Cytofluorographic evidence thatthymocyte dipeptidyl peptidase IV (CD26) activity is altered with stage of ontogeny and apoptotic status," *Cytometry* 23: 322–329.

Sanderink, G.J., et al., 1988, Human Aminopeptidases: A Review of the Literature. *J. Clin. Chem. Clin. Biochem.* 26: 795–807.

Schon, E. et al., "The role of dipeptidyl peptidase IV in human T lymphocyte activation. Inhibitors and antibodies against dipeptidyl peptidase IV suppress lymphocyte proliferation and immunoglobulin synthesis in vitro," *Eur. J. Immunol.* Dec. 1987;17(12):1821–6.

Stein, R.L. et al. 1987, "Catalysis by human leukocyte elastase: Mechanistic insights into specificity requirements," *Biochem.* 26:1301–1305.

Stein, R.L. et al. 1987, "Catalysis by human leukocyte elastase: Proton inventory as a mechanistic probe," *Biochem.* 26:1305–1314.

Tanaka, T. et al., 1993, "The costimulatory activity of the CD26 antigen requires dipeptidyl peptidase IV enzymatic activity," *Proc. Natl. Acad. Sci. USA* 90:4586–4590.

Thiele, D.L. et al., 1990, "Mechanism of L–leucyl–L–leucine methyl ester–mediated killing of cytotoxic lymphocytes: Dependence on a lysosomal thiol protease, dipeptidyl peptidase I, that is enriched in these cells," *Proc. Natl. Acad. Sci. USA* 87: 83–87.

Weiss, S.J. 1989, "Tissue destruction by neutrophils," *N. Eng. J. Med.* 320: 365–376.

Whitlock, C.A., et al., 1987. "Bone marrow stromal cell lines with lymphopoietic activity express high levels of pre–B neoplasia–associated molecule," *Cell* 48: 1009–1021.

Woessner, J.F. Jr., 1991, "Matrix metalloproteinases and their inhibitors in connective tissue remodeling," *FASEB J.* 5: 2145–2154.

Wu, Q. et al., 1991. "Aminopeptidase A activity of the murine B–lymphocyte differentiation antigen BP–1/6C3," *Proc. Natl. Acad. Sci, USA* 88: 676–680.

* cited by examiner

METHOD AND APPARATUS FOR INCREASING THE DYNAMIC RANGE AND ACCURACY OF BINDING ASSAYS

FIELD OF THE INVENTION

This invention relates to methods for increasing the dynamic range and accuracy of assays, especially binding assays. The invention further relates to apparatus capable of implementing such methods.

BACKGROUND OF THE INVENTION

Biochemical and biological assays are designed to test for activity in a broad range of systems ranging from protein-protein interactions, enzyme catalysis, small molecule-protein binding, to cellular functions.

In general, fluorescent, chemiluminecent and other assay formats comprise three distinguishable response ranges. Where the amount of analyte being assayed is within the dynamic range of the assay, the reported signal will be dependent upon the amount of analyte present. Where the amount of analyte exceeds the dynamic range of the assay, saturation will occur and the reported signal will not be indicative of the true analyte concentration. Likewise, where the amount of analyte present in the sample falls below the threshold of the assay's dynamic range, the assay may be insufficiently sensitive to the actual analyte concentration, and the reported signal will also not be indicative of the true analyte concentration.

Two approaches have conventionally been employed to address this problem. In the first, multiple dilutions or concentrations of a sample are made and then assayed for a defined time period and the results are evaluated against that of a "standard curve" of assay results obtained with analyte of varying but known concentration. In the second approach, an amount of sample is assayed for multiple times, and results falling within the dynamic range of the assay are used to calculate the analyte's concentration (see, for example, U.S. Pat. No. 5,306,468 (Anderson et al.), U.S. Pat. No. 6,212,291 (Wang et al.)).

U.S. Pat. Nos. 6,270,695; 6,218,137; 6,139,782; 6,090,571 and 6,045,727 (Akhavan-Tafti, et al.) and U.S. Pat. Nos. 6,045,991; 5,965,736; 6,580,963 and 5,772,926 (Akhavan-Tafti) indicate the possibility of making multiple exposures in chemiluminescent assays. The use of multiple exposures in photography is also known (see, for example, U.S. Pat. No. 6,177,958 (Anderson) and U.S. Pat. No. 5,754,229 (Elabd)).

Microtiter or multi-well plates are becoming increasingly popular in various chemical and biological assays. High-density format plates, such as 384, 864 and 1536 well plates, are beginning to displace 96-well plates as the plate of choice. Many of the assays conducted in multiwell plates employ some type of light detection from the plate as the reporter for positive or negative assays results. Such assays include fluorescence assays, chemiluminescence assays (e.g., luciferase-based assays), phosphorescence assays, scintillation assays, and the like. In particular, with the advent of solid phase scintillating materials, capsules and beads, homogeneous scintillation proximity assays (SPA) are now being performed with increasing frequency in multiwell plates.

Detection of light signals from multiwell plates in the past has typically been done using plate readers, which generally employ a photodetector, an array of such photodetectors, photomultiplier tubes or a photodiode array to quantify the amount of light emitted from different wells. Such plate readers have been disclosed, for example, by (U.S. Pat. No. 4,810,096 (Russell, et al.) and (U.S. Pat. No. 5,198,670 (VanCauter, et al.)). Although plate readers can detect the total light from each well, they have a number of limitations. For example, plate readers are typically not capable of resolving discrete light sources in a single well, so they could not be used, for example, to differentiate light from different beads in one well. Further, most plate readers have fewer photodetectors than there are wells in the plate, so at least some wells must be read serially, adding to the time required to complete the assays. This becomes a substantial problem in assays where the light signal is so low that each well needs to be in the detection field for an extended period of time (e.g., tens of minutes). In addition, most currently-available plate readers have been designed for 96-well plates. Although some can be adapted for, e.g., 384-well plates, the adaptation does not result in any significant increase in throughput, since a 384-well plate going through a modified 96-well reader typically takes four times as long to read as a 96-well plate.

Another technique that has been applied to the detection of light from multiwell plates is imaging. Prior art imaging systems typically comprise a standard 50–55 mm f1.4 photographic lens coupled to a camera. While such systems can be used to image an entire multiwell plate, and theoretically provide resolution of discrete light points within individual wells, they have poor sensitivity, even when coupled to efficient cameras, so that many assays still require imaging times of tens of minutes or more. Other assays, such as SPA bead-based assays, cannot be performed at all due to lack of sensitivity. Further, images acquired with such systems suffer from vignetting and lateral distortion effects, making it difficult or impossible to compare signals from center portions of the plate with signals from lateral wells.

The demand for increased throughput during primary screening using less reagent is changing the way of drug discovery. High throughput screening in 96-well format plates is being replaced by the use of higher density plates, such as 384 and 1536-well formats. The analysis of radio-metric assays by scintillation counters is becoming limiting since only 12 wells can be counted at a time. (Manzella S. M., et al. "A biphasic radiometric assay of glycogenin using the hydrophobic acceptor n-dodecyl-beta-D-maltoside," Anal. Biochem. 1994 Feb. 1;216(2):383–91) (West B. C., et al. "Neutrophil uptake of vaccinia virus in vitro," J. Infect. Dis. 1987 Octber ;156(4):597–606) (Boonkitticharoen V., et al. "Radiometric assay of bacterial growth: analysis of factors determining system performance and optimization of assay technique," J. Nucl. Med. 1987 February;28(2): 209–170).

Charge coupled devices (CCD) use a light-sensitive integrated circuit to store and display data for an image in such a way that each pixel (picture element) in the image is converted into an electrical charge, the intensity of which is related to a color in the color spectrum. Such devices have found use in chemical assays and radiologic imaging (see, for example, U.S. Pat. No. 5,306,468 (Anderson et al.), U.S. Pat. No. 6,212,291 (Wang et al.).

A CCD reads the light emitted through the electrode and the signal is sent to a microprocessor which converts the signal to the desired readout form. Data obtained (and, optionally, recorded) by the detection device is typically processed, e.g., by digitizing the image and storing and analyzing the image on a computer readable medium. A variety of commercially available peripheral equipment and software is available for digitizing, storing and analyzing a signal or image. For example, real-time binding and dissociation can be monitored visually or by video imaging, such as with a CCD camera and frame grabber software (U.S. Pat. No. 5,599,668 (Stimpson, et al.; U.S. Pat. No. 5,843,651 (Stimpson, et al.)).

CCD cameras are used for many applications in biochemistry and medicine (Dujardin F. H., et al., "Quantitative assessment of cortical bone remodelling from routine radiographs of total hip arthroplasty," Med.Eng. Phys. 1996 September; 18(6): 489–94; Houze T. A., et al., "Detection of thymidylate synthase gene expression levels in formalin-fixed paraffin embedded tissue by semiquantitative, nonradioactive reverse transcriptase polymerase chain reaction," Tumour Biol. 1997;18(1):53–68); Innocenti B., et al., "Imaging extracellular waves of glutamate during calcium signaling in cultured astrocytes," J. Neurosci. 2000 Mar. 1;20(5):1800–8; Katanec D, et al., "Computer assisted densitometric image analysis (CADIA) of bone density in periradicular bone defects healing," Coll Antropol—1998 December; 22 Suppl: 7–13; Nilsson H, et al., "Laser-induced fluorescence studies of the biodistribution of carotenoporphyrins in mice," Br. J. Cancer 1997;76(3):355–64; O'Rourke B, et al., "High-speed digital imaging of cytosolic $Ca2+$ and contraction in single cardiomyocytes," Am J Physiol 1990 July;259(1 Pt 2):H230–42); Peng Q., et al., "Correlation of distribution of sulphonated aluminium phthalocyanines with their photodynamic effect in tumour and skin of mice bearing CaD2 mammary carcinoma," Br. J. Cancer 1995 September;72(3):565–74; Pope A. J., et al., "The detection of phthalocyanine fluorescence in normal rat bladder wall using sensitive digital imaging microscopy," Br. J. Cancer 1999 November;64(5):875–9; Yasui T, et al., "Imaging of *Lactobacillus brevis* single cells and microcolonies without a microscope by an ultrasensitive chemiluminescent enzyme immunoassay with a photon-counting television camera," Appl. Environ. Microbiol. 1997 November;63(11):4528–33; Zhang J. H., et al. "Development of a carbon dioxide-capture assay in microtiter plate for aspartyl-beta-hydroxylase," Anal. Biochem. 1999 Jul. 1;271(2):137–42).

Although methods involving multiple exposure times have been used to identify the optimum desired exposure time in enzymatic assays, a need remains for automatable methods that can be used to process simultaneously not only multiple samples, but also multiple signal generation foci within each sample, each potentially reporting differing signals in the assay. The present invention addresses this need.

SUMMARY OF THE INVENTION

This invention relates to methods for increasing the dynamic range and accuracy of assays in which the presence or absence of a light signal is used to assay for the presence, absence, or concentration of a target analyte. The invention additionally relates to the embodiment of such methods in which a change (i.e., an evolution or loss) of the light signal in two or more time intervals is used to assay for the presence, absence, or concentration of the target analyte. The invention further relates to apparatus capable of implementing such methods. The invention is particularly amenable for us in increasing the dynamic range and accuracy of binding assays.

In its preferred embodiments, the present invention provides a method to increase the dynamic range of a binding assay, utilizing multiple exposure or integration times. In the case of assays that are quantitated from an image generated by a CCD camera, the method involves the use of multiple exposures of the assay, each with a different exposure time. Samples that give weak signals can be detected and quantitated using a relatively longer exposure, while samples from the same assay that give strong signals can be detected and quantitated using a relatively shorter exposure. The process of taking multiple exposures, and the analysis of the multiple images, including the selection of the proper exposure to use to quantitate any one particular sample, is preferably automated. Since, for those samples that give a midrange signal, each exposure represents an independent measurement of the binding assay, this method permits an increase in both the precision and accuracy of the assay.

In detail, the invention concerns a method for enhancing the dynamic range of an assay of the presence, absence, activity or concentration of two or more target analytes in one or more samples wherein the presence, absence, activity or concentration of the target analytes is assayed by the emission or quenching of a light signal, wherein the method comprises the steps:

(A) conducting an assay for the presence, absence, activity or concentration of each of the target analytes in the one or more samples wherein the assays each cause light signals to be emitted or quenched;

(B) employing a computer system comprising a CCD camera detector to detect the light signals, and to generate data corresponding to the detected signals; and (C) causing the computer system to compare the generated data using data corresponding to the light signal generated by a known concentration of the target analyte in a known dynamic range of the assay and report the presence, absence, activity or concentration of the target analyte; wherein the computer system causes the CCD camera detector to independently detect sufficient light signal for each of the target analytes to ensure that the reported presence, absence, activity or concentration of each target analyte is determined using data corresponding to a light signal that is within the known dynamic range of the assay for that target analyte.

The invention additionally concerns the embodiment of such method wherein, for at least one of the target analytes, the computer system causes the CCD camera detector to detect light signal cumulatively until a total detected light signal is obtained that is within the known dynamic range of the assay for the target analyte; and wherein the total detected light signal is used to determine the presence, absence, activity or concentration of the target analyte, as well as the embodiment of such method wherein, for at least one of the target analytes, the computer system causes the CCD camera detector to detect light signal discontinuously at more than one time interval so that a detected light signal is obtained that is within the known dynamic range of the assay for the target analyte; and wherein the detected light signal that is within the known dynamic range of the assay for the target analyte is used to determine the presence, absence, activity or concentration of the target analyte.

The invention additionally concerns the embodiments of such methods wherein the computer system stores the cumulative change in the light signal in two or more of the time intervals. The invention additionally concerns the embodiments of such methods wherein the method assays the presence, absence, activity or concentration of more than one target analyte in a sample, and particularly wherein the method simultaneously or sequentially assays the presence, absence, activity or concentration of the more than one target analyte in a sample. The invention additionally concerns the embodiments of such methods wherein the step (D) is performed simultaneously or sequentially for each target analyte being assayed.

The invention further concerns the embodiments of such methods wherein the target analytes are enzymes or other proteins whose expression is characteristic of disease (e.g., bone specific alkaline phosphatase, aldose reductase, myoglobin, troponin I, etc.); or co-factors (including vitamins, such as vitamin B12, folate, $T_3$, $T_4$, TU, $FT_3$, $FT_4$, etc.), drugs or metabolites (including anti-cancer drugs, chemotherapeutic drugs, anti-viral drugs, non-steroidal anti-inflammatory drugs (NSAID), steroidal anti-inflammatory drugs, anti-fungal drugs, detoxifying drugs, analgesics, bronchodilators, anti-bacterial drugs, antibiotic drugs, diuretics, digoxin, anti-metabolites, calcium channel blockers, drugs for treatment of psoriasis, substances of abuse (e.g., cocaine, opiates, and other narcotics), pesticides, herbicides, etc.), cell-surface receptors (including protein-tyrosine kinase receptors (e.g., EGFR, PDGFR, MCSFR, SCFR, insulin-R, VEGFR, Trk, Met, Ron, Axl, Eph); or cell-surface receptors (e.g., receptors for TNF and related factors (e.g., Trk, Met, Ron, Axl, Eph, Fas, TNFRI, TNFRII, CD40, CD30, CD27, 4-1BB, LNGFR, OX40), serine-threonine kinase receptors (e.g., TGFβR), transmembrane 7 or G protein-coupled receptor families (e.g., CCR1, CCR2α, β, CCR3, CCR4, CCR5, CXCR1, CXCR2, CXCR3, CXCR4, BLR1, BLR2, V28, and class I and class II cytokines), receptors such as CD4, class I (hematopoietic cytokine) receptors (e.g., IL-1β, IL-2R β and γ chains, IL-3Rα, IL-5Rα, GMCSFRα, the IL-3/IL-5/GM-CSF receptor common β-chain, IL-4Rα, IL-7Rα, IL-9Rα, IL-10R, IL-11Rα, IL-13Rα, LIFR β, TPOR, OBR, IL-6Rα, gp130, OSMRβ, GCSFR, IL-11Rα, IL-12Rb1 and IL-12Rb2, GHR, PRL, and EPO), EGFR, PDGFR, MCSFR, SCFR, insulin-R, VEGFR, and class II receptors (e.g., IFNgRα, IFNgRβ, IL-10R, tissue factor receptor (TFR), and IFNαR1), etc.); or hormones (such as adrenaline (epinephrine), adrenocorticotropic hormone (ACTH), androgens (e.g., testosterone), angiotensinogen, antidiuretic hormone (ADH) (vasopressin), atrial-natriuretic peptide (ANP), calciferol (vitamin D3), calcitonin, calcitriol, cholecystokinin, chorionic gonadotropin (CG), dopamine, erythropoietin, estrogens (e.g., estradiol), follicle-stimulating hormone (FSH), gastrin, glucagon, glucocorticoids (e.g., cortisol and urinary cortisol), gonadotropin-releasing hormone (GnRH), gorticotropin-releasing hormone (CRH), growth hormone (GH), growth hormone-releasing hormone (GHRH), insulin, insulin-like growth factor-1 (IGF-1), leptin, luteinizing hormone (LH), melatonin, mineralocorticoids (e.g., aldosterone), neuropeptide Y, noradrenaline (norepinephrine), oxytocin, parathyroid hormone (PTH), progesterone, prolactin (PRL), renin, secretin, somatostatin, theophylline, thiiodothyronine T3, thrombopoietin, thyroid-stimulating hormone (TSH), thyrotropin-releasing hormone (TRH), thyroxine (T4); or cytokines (such as the interleukins ("IL") (e.g., IL-2, IL-3, IL-4, IL-5, IL-6, IL-7, IL-8, IL-10, IL-12, IL-13) or TNFα ("Tumor Necrosis Factor"), VEGF ("Vascular Endothelial Growth Factor"), GMCSF ("Granulocyte-Macrophage Colony-Stimulating Factor"), IL-1βFGF β ("Fibroblast Growth Factor-β"), INFγ ("Interferon-γ"), EGF ("Epidermal Growth Factor"), PDGF ("Platelet-Derived Growth Factor"), MCSF ("Macrophage Colony-Stimulating Factor"), SCF ("Stem Cell Factor"), insulin, VEGF (Vascular Endothelial Growth Factor), Trk ("Tyrosine Kinase"), Met ("Hepatocyte Growth Factor"), Ron ("Macrophage Stimulating Protein receptor"), Axl ("ufo gene"), Eph ("Ephrin"), Fas ("Tumor Necrosis Factor Receptor Superfamily, member 6"), CD40 ("Tumor necrosis factor receptor superfamily member 5"), CD30 ("Tumor Necrosis Factor Receptor Superfamily member 8"), CD27 ("Tumor necrosis factor receptor superfamily member 7"), 4-1BB (Tumor necrosis factor receptor superfamily member 9), LNGFR ("Low Affinity Nerve Growth Factor Receptor"), OX40 ("Tumor necrosis factor receptor superfamily member 4"), TGFβR ("Transforming Growth Factor-Beta"), CCR1, CCR2α, β, CCR3, CCR4, CCR5, CXCR1, CXCR2, CXCR3, CXCR4, ("Chemokine Receptors"), BLR1, BLR2 ("Burkitt Lymphoma Receptor"), V28 receptor ("Fractalkine receptor"), or a receptor of IL-2, IL-3, IL-4, IL-5, IL-6, IL-7, IL-8, IL-10, IL-12, or IL-13 ("Interleukins"); or antigens (such as those characteristic of Chlamydia, i Streptococcus pyogenesGroup A bacteria, *H. pylori*, or *M. tuberculosi*, hepatitis virus, rubella, CMV or immunodeficiency virus (HIV, FIV), prostate specific antigen, etc.); or antibodies to such antigens, or autoimmune immunoglobulins, thyroglobulin, anti-thyroglobulin, IgE, IgG, or IgM immunoglobulins, tumor markers (e.g., prostate specific antigen, AFP CEA, etc.).

The invention further concerns the embodiments of such methods wherein the light signal or the change in light signal is an evolution or loss of a fluorescent light signal, a chemiluminescent light signal, an ultraviolet light signal, or a visible wavelength light signal.

The invention further concerns an apparatus for enhancing the dynamic range of an assay of the presence, absence, activity or concentration of two or more target analytes in one or more samples, wherein the presence, absence, activity or concentration of the target analytes is assayed by the emission or quenching of a light signal, the apparatus comprising:

(A) one or more containers for receiving a portion of the one or more samples, the containers additionally containing assay reagents comprising a compound that, in response to the presence of a target analyte causes a detectable light signal; and (B) a computer system comprising a CCD camera detector, the computer system being specially adapted to detect the light signal and generate data corresponding to the detected signal; the computer system additionally processing a capability for comparing the generated data with data corresponding to the light signal generated by a known concentration of the target analyte in a known dynamic range of the assay and report the presence, absence, activity or concentration of the target analyte; wherein the computer system causes the CCD camera detector to independently detect sufficient light signal for each of the target analytes to ensure that the reported presence, absence, activity or concentration of each target analyte is determined using data corresponding to a light signal that is within the known dynamic range of the assay for that target analyte.

The invention additionally concerns the embodiment of such apparatus wherein, for at least one of the target analytes, the computer system causes the CCD camera detector to detect light signal cumulatively until a total detected light signal is obtained that is within the known dynamic range of the assay for the target analyte; and wherein the total detected light signal is used to determine the presence, absence, activity or concentration of the target analyte, as well as the embodiment of such apparatus wherein, for at least one of the target analytes, the computer system causes the CCD camera detector to detect light signal discontinuously at more than one time interval until a detected light signal is obtained that is within the known dynamic range of the assay for the target analyte; and wherein the detected light signal that is within the known dynamic range of the assay for the target analyte is used to determine the presence, absence, activity or concentration of the target analyte.

The invention additionally concerns the embodiment of such apparatus wherein the computer system stores the cumulative change in the light signal in two or more of the time intervals.

The invention additionally concerns the embodiment of such apparatus wherein the apparatus assays the presence, absence, activity or concentration of more than one target analyte in the same sample, especially wherein the apparatus simultaneously or sequentially assays the presence, absence, activity or concentration of the more than one target analyte in the same sample.

The invention additionally concerns the embodiment of such apparatus wherein the step (D) is performed simultaneously or sequentially for each target analyte being assayed.

The invention additionally concerns the embodiment of such apparatus wherein the one or more containers is a multi-well microtiter plate.

The invention additionally concerns the embodiment of such apparatus wherein the target analyte has an activity and wherein the computer system additionally calculates the rate of a target analyte activity in the sample.

The invention additionally concerns the embodiment of such apparatus wherein the target analyte is selected from the group consisting of an enzyme, a co-factor, a receptor, a receptor ligand, a hormone, a cytokine, a blood factor, a virus, an antigen, a steroid, a drug, and an antibody.

The invention further concerns the embodiments of such apparatus wherein the light signal or the change in light signal is an evolution or quenching (loss) of a fluorescent, chemiluminescent, ultraviolet, or visible wavelength light signal.

The invention particularly concerns the embodiments of such apparatus wherein multiple analytes are assayed in a single container (either simultaneously or sequentially) as well as wherein a single analyte is assayed in a single container.

The invention further concerns the embodiments of such apparatus wherein the target analytes are enzymes or other proteins whose expression is characteristic of disease (e.g., bone specific alkaline phosphatase, aldose reductase, myoglobin, troponin I, etc.); or co-factors (including vitamins, such as vitamin B12, folate, $T_3$, $T_4$, TU, $FT_3$, $FT_4$, etc.), drugs or metabolites (including anti-cancer drugs, chemotherapeutic drugs, anti-viral drugs, non-steroidal anti-inflammatory drugs (NSAID), steroidal anti-inflammatory drugs, anti-fungal drugs, detoxifying drugs, analgesics, bronchodilators, anti-bacterial drugs, antibiotic drugs, diuretics, digoxin, anti-metabolites, calcium channel blockers, drugs for treatment of psoriasis, substances of abuse (e.g., cocaine, opiates, and other narcotics), pesticides, herbicides, etc.), cell-surface receptors (including protein-tyrosine kinase receptors (e.g., EGFR, PDGFR, MCSFR, SCFR, insulin-R, VEGFR, Trk, Met, Ron, Axl, Eph); or cell-surface receptors (e.g., receptors for TNF and related factors (e.g., Trk, Met, Ron, Axl, Eph, Fas, TNFRI, TNFRII, CD40, CD30, CD27, 4-1BB, LNGFR, OX40), serine-threonine kinase receptors (e.g., TGFβPR), transmembrane 7 or G protein-coupled receptor families (e.g., CCR1, CCR2α, β, CCR3, CCR4, CCR5, CXCR1, CXCR2, CXCR3, CXCR4, BLR1, BLR2, V28, and class I and class II cytokines), receptors such as CD4, class I (hematopoietic cytokine) receptors (e.g., IL-1β, IL-2R β and γ chains, IL-3Rα, IL-5Rα, GMCSFRα, the IL-3/IL-5/GM-CSF receptor common β-chain, IL-4Rα, IL-7Rα, IL-9Rα, IL-10R, IL-11Rα, IL-13Rα, LIFR β, TPOR, OBR, IL-6Rα, gp130, OSMRβ, GCSFR, IL-11Rα, IL-12Rb1 and IL-12Rb2, GHR, PRL, and EPO), EGFR, PDGFR, MCSFR, SCFR, insulin-R, VEGFR, and class II receptors (e.g., IFNgRα, IFNgRβ, IL-10R, tissue factor receptor (TFR), and IFNαR1), etc.); or hormones (such as adrenaline (epinephrine), adrenocorticotropic hormone (ACTH), androgens (e.g., testosterone), angiotensinogen, antidiuretic hormone (ADH) (vasopressin), atrial-natriuretic peptide (ANP), calciferol (vitamin D3), calcitonin, calcitriol, cholecystokinin, chorionic gonadotropin (CG), dopamine, erythropoietin, estrogens (e.g., estradiol), follicle-stimulating hormone (FSH), gastrin, glucagon, glucocorticoids (e.g., cortisol and urinary cortisol), gonadotropin-releasing hormone (GnRH), gorticotropin-releasing hormone (CRH), growth hormone (GH), growth hormone-releasing hormone (GHRH), insulin, insulin-like growth factor-1 (IGF-1), leptin, luteinizing hormone (LH), melatonin, mineralocorticoids (e.g., aldosterone), neuropeptide Y, noradrenaline (norepinephrine), oxytocin, parathyroid hormone (PTH), progesterone, prolactin (PRL), renin, secretin, somatostatin, theophylline, thiiodothyronine T3, thrombopoietin, thyroid-stimulating hormone (TSH), thyrotropin-releasing hormone (TRH), thyroxine (T4); or cytokines (such as the interleukins (e.g., IL-2, IL-3, IL-4, IL-5, IL-6, IL-7, IL-8, IL-10, IL-12, IL-13) or TNFα, VEGF, GMCSF, IL-1β, FGFβ, INFγ, EGF, PDGF, MCSF, SCF, insulin, VEGF, Trk, Met, Ron, Axl, Eph, Fas, CD40, CD30, CD27, 4-1BB, LNGFR, OX40, TGFβR, or a ligand of CCR1, CCR2α, β, CCR3, CCR4, CCR5, CXCR1, CXCR2, CXCR3, CXCR4, BLR1, BLR2, V28 receptor, or a receptor of IL-2, IL-3, IL-4, IL-5, IL-6, IL-7, IL-8, IL-10, IL-12, or IL-13; or antigens (such as those characteristic of Chlamydia, *Streptococcus pyogenes* Group A bacteria, *H. pylori*, or *M. tuberculosi*, hepatitis virus, rubella, CMV or immunodeficiency virus (HIV, FIV), prostate specific antigen, etc.); or antibodies to such antigens, or autoimmune immunoglobulins, thyroglobulin, anti-thyroglobulin, IgE, IgG, or IgM immunoglobulins, tumor markers (e.g., prostate specific antigen, AFP CEA, etc.).

The invention further concerns the embodiments of such apparatus wherein the light signal or the change in light signal is an evolution or loss of a fluorescent light signal, a chemiluminescent light signal, an ultraviolet light signal, or a visible wavelength light signal.

DESCRIPTION OF THE PREFERRED EMBODIMENTS

This invention relates to methods for increasing the dynamic range and accuracy of assays in which a light signal is used to assay for the presence, absence, or concentration of a target analyte. The invention further relates to apparatus capable of implementing such methods. The invention is particularly amenable for us in increasing the dynamic range and accuracy of binding assays.

As used herein, the term "dynamic range" is intended to denote the range of target analyte concentration in which the detected light signal (or a change of the light signal) is dependent upon the concentration of the target analyte.

As used herein, the term "target analyte" is intended to denote a compound or compounds whose presence, absence or concentration are the object of the assay. Virtually any compound can be employed as a target analyte in the presence invention. Without limitation, such analytes may be enzymes, co-factors, receptors, receptor ligands, hormones, cytokines, blood factors, viruses, antigens, steroids, drugs, antibodies, etc. For example, the target analytes of the present invention may include:

enzymes or other proteins whose expression is characteristic of disease (e.g., bone specific alkaline phosphatase, aldose reductase, myoglobin, troponin I, etc.);

drugs or metabolites (e.g., anti-cancer drugs, chemotherapeutic drugs, anti-viral drugs, non-steroidal anti-inflammatory drugs (NSAID), steroidal anti-inflammatory drugs, anti-fungal drugs, detoxifying drugs, analgesics, bronchodilators, anti-bacterial drugs, antibiotic drugs, diuretics, digoxin, anti-metabolites, calcium channel blockers, drugs for treatment of psoriasis, substances of abuse (e.g., cocaine, opiates, and other narcotics), pesticides, herbicides, etc.);

co-factors (including vitamins, such as vitamin B12, folate, $T_3$, $T_4$, TU, $FT_3$, $FT_4$, etc.);

cell-surface receptors (e.g., receptors for TNF and related factors (e.g., Trk, Met, Ron, Axl, Eph, Fas, TNFRI, TNFRII, CD40, CD30, CD27, 4-1BB, LNGFR, OX40), serine-threonine kinase receptors (e.g., TGFβR), transmembrane 7 or G protein-coupled receptor families (e.g., CCR1, CCR2α, β, CCR3, CCR4, CCR5, CXCR1, CXCR2, CXCR3, CXCR4, BLR1, BLR2, V28, and class I and class II cytokines), receptors such as CD4, class I (hematopoietic cytokine) receptors (e.g., IL-1β, IL-2R β and γ chains, IL-3Rα, IL-5Rα, GMCSFRα, the IL-3/IL-5/GM-CSF receptor common β-chain, IL-4Rα, IL-7Rα, IL-9Rα, IL-10R, IL-11Rα, IL-13Rα, LIFR β, TPOR, OBR, IL-6Rα, gp130, OSMRβ, GCSFR, IL-11Rα, IL-12Rb1 and IL-12Rb2, GHR, PRL, and EPO), EGFR, PDGFR, MCSFR, SCFR, insulin-R, VEGFR, and class II receptors (e.g., IFNgRα, IFNgRβ, IL-10R, tissue factor receptor (TFR), and IFNαR1), etc.);

hormones (such as adrenaline (epinephrine), adrenocorticotropic hormone (ACTH), androgens (e.g., testosterone), angiotensinogen, antidiuretic hormone (ADH) (vasopressin), atrial-natriuretic peptide (ANP), calciferol (vitamin D3), calcitonin, calcitriol, cholecystokinin, chorionic gonadotropin (CG), dopamine, erythropoietin, estrogens (e.g., estradiol), follicle-stimulating hormone (FSH), gastrin, glucagon, glucocorticoids (e.g., cortisol and urinary cortisol), gonadotropin-releasing hormone (GnRH), gorticotropin-releasing hormone (CRH), growth hormone (GH), growth hormone-releasing hormone (GHRH), insulin, insulin-like growth factor-1 (IGF-1), leptin, luteinizing hormone (LH), melatonin, mineralocorticoids (e.g., aldosterone), neuropeptide Y, noradrenaline (norepinephrine), oxytocin, parathyroid hormone (PTH), progesterone, prolactin (PRL), renin, secretin, somatostatin, theophylline, thiiodothyronine T3, thrombopoietin, thyroid-stimulating hormone (TSH), thyrotropin-releasing hormone (TRH), thyroxine (T4);

cytokines (such as the interleukins (e.g., IL-2, IL-3, IL-4, IL-5, IL-6, IL-7, IL-8, IL-10, IL-12, IL-13) or TNFα, VEGF, GMCSF, IL-1β, FGFβ, INFγ, EGF, PDGF, MCSF, SCF, insulin, VEGF, Trk, Met, Ron, Axl, Eph, Fas, CD40, CD30, CD27, 4-1BB, LNGFR, OX40, TGFβR, or a ligand of CCR1, CCR2α, CCR3, CCR4, CCR5, CXCR1, CXCR2, CXCR3, CXCR4, BLR1, BLR2, V28 receptor, or a receptor of IL-2, IL-3, IL-4, IL-5, IL-6, IL-7, IL-8, IL-10, IL-12, or IL-13;

antigens (such as those characteristic of Chlamydia, *Streptococcus pyogenes* Group A bacteria, *H. pylori*, or *M. tuberculosi*, hepatitis virus, rubella, CMV or immunodeficiency virus (HIV, FIV), prostate specific antigen, etc.); or antibodies to such antigens, or autoimmune immunoglobulins, thyroglobulin, anti-thyroglobulin, IgE, IgG, or IgM immunoglobulins, tumor markers (e.g., prostate specific antigen, AFP CEA, etc.).

The present invention comprises a method to increase the dynamic range of such binding assays by utilizing multiple exposure or signal-integration times. In a preferred embodiment, the binding assays will involve the change of a detectable fluorescent, chemiluminescent, colorimetric, radiological, nephelometric, turbidometric, ultraviolet, or other signal in response to the presence or absence of the analyte that is the target of the assay.

In a further embodiment, the presence, absence, or concentration of a target analyte will be assayed by a change (i.e., by the evolution or loss) of a light signal in two or more time intervals. As used herein, the term "change" of a detectable signal is intended to include both processes resulting in an increase in signal (for example, as when a fluorescent product is produced over time as a consequence of the action of a target enzyme) as well as processes resulting in a decrease in signal (for example, as when a fluorescent substrate is consumed over time as a consequence of the action of a target enzyme). In accordance with the methods of the present invention, the detected light signal may involve light of the visible, near-UV, or UV wavelengths, and may be generated by chemiluminescent, fluorescent (including laser induced fluorescent), colorimetric, radiological, nephelometric, turbidometric or other mechanism (for example through the use of analytes and substrates that emit or quench such light signal in response to the presence, absence or concentration of the target analyte).

Any of a wide variety of such analytes and substrates may be used in accordance with the principles of the present invention in order to generate such light signal. In one embodiment, such analytes and substrates may possess a chemiluminescent moiety. Suitable chemiluminescent moieties include acridinium esters, ruthenium complexes, metal complexes (e.g., U.S. Pat. Nos. 6,281,021, 5,238,108 and 5,310,687), oxalate ester-peroxide combination, etc.)

Alternatively, such analytes and substrates may possess a colorimetric moiety. Suitable colorimetric moieties include thiopeptolides, anthroquinone dyes, 2 methoxy 4 (2 nitrovinyl)phenyl β-2 acetamido 2 deoxy β D glucopyranoside; ammonium 5 [4 (2 acetamido 2 deoxy β D glucopyranosyloxy) 3 methoxy phenylmethylene] 2 thioxothiazolin 4 one 3 ethanoate hydrate; 4{2 [4 (β D glucosyl pyranosyloxy) 3methoxy phenyl]vinyl} 1 methylquinolinium iodide, 2 methoxy 4 (2 nitrovinyl)phenyl β D galactopyranoside, 2 {2 [4 (β D galactopyranosyloxy)3 methoxyphenyl]vinyl} 1 methyl quinolinium iodide, 2 {2 [4 (β D galactopyranosyloxy)3 methoxyphenyl]vinyl} 3 methyl benzothiazolium iodide, 2 {2 [4 (β D glucopyranosyloxy) 3 methoxyphenyl]vinyl} 1 methyl quinolinium iodide, 2 {2 [4 (β D glucopyranosyloxy) 3 methoxyphenyl]vinyl} 1 propyl quinolinium iodide, 2 {2 [4 (β D glucopyranosyloxy) 3 methoxyphenyl]vinyl} 3 methyl benzothiazolium iodide, ammonium 5 [4 β D glucopyranosyloxy) 3 methoxy phenylmethylene] 2 thioxothiazolin 4 one 3 ethanoate hydrate, 2 methoxy 4 (2 nitrovinyl) phenyl acetate, 2 methoxy 4 (2 nitrovinyl) phenyl propionate, 5 [4 propanoyloxy) 3,5 dimethoxy phenylmethylene] 2 thioxothiazolin 4 one 3 ethanoate, 5 [4 butanoyloxy) 3,5 dimethoxy phenylmethylene] 2 thioxothiazolin 4 one 3 ethanoate, 5 [4 decanoyloxy) 3,5 dimethoxy phenylmethylene] 2 thioxothiazolin 4 one 3 ethanoate, 5 [4 dodecanoyloxy) 3,5 dimethoxy phenylmethylene] 2 thioxothiazolin 4 one 3 ethanoate, 5 [4 tetradecanoyloxy) 3,5 dimethoxy phenylmethylene] 2 thioxothiazolin 4 one 3 ethanoate, Pyridinium 4 {2 [4 (phosphoroyloxy) 3,5 dimethoxyphenyl]vinyl} 1 propyl quinolinium iodide, Pyridinium 5 (4 phosphoryloxy 3,5 dimethoxy phenylmethylene) 3 methyl 2 thioxothiazolin 4 one, etc.

Preferably, however, the detected light will be fluorescent, and the analytes and substrates will possess a fluorescence-generating moiety whose fluorescence is dependent upon the presence, absence or concentration of the target analyte. Examples of suitable fluorescence-generating moieties include rhodamine 110; rhodol; coumarin or a fluorescein compound. Derivatives of rhodamine 110, rhodol, or fluorescein compounds that have a 4' or 5' protected carbon may likewise be employed. Preferred examples of such compounds include 4'(5')thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-carboxyrhodamine 110, 4'(5')-chlororhodamine 110, 4'(5')-methylrhodamine 110, 4'(5')-sulforhodamine 110 and 4'(5')thiorhodamine 110. "4' (5')" means that at the 4 or 5' position the hydrogen atom on the carbon atom is substituted with a specific organic group or groups as previously listed. A 7-Amino, or sulfonated coumarin derivative may likewise be employed.

In a further embodiment, cellprobe reagents may be employed as the analyte or substrate. In general such cell-probe reagents contain an "indicator group" and one, two, three, four or even more "leaving groups." The "indicator group" of the compound is a chemical moiety selected for its ability to have a first state when joined to the leaving group, and a second state when the leaving group is cleaved from the indicator group by the enzyme. The indicator group is preferably excitable (caused to fluoresce) at a wavelength about the visible range, for example, at wavelength between about 450 to 500 nanometers (nm). The indicator group will usually emit in the range of about 480 to 620 nm, preferably 500 to 600 nm and more preferably 500 to 550 nm. Autofluorescence of the cell is most prevalent below about 500 nm. The indicator group is preferably derived from fluorescent, colorimetric, bioluminescent or chemiluminescent compounds. The indicator group is preferably quenched when joined to the leaving group. The term quenched means that the indicator group has substantially less fluorescence or chemiluminescence when joined to the leaving group compared to its fluorescence or chemiluminescence after the leaving group has been cleaved. For example, the enzyme glutamyltranspeptidase reacts with gammaglutamyl amino acid peptide giving gamma glutamic acid; trypsin cleaves the peptide at the arginine residue; aminopeptidase-M hydrolyzes the peptide at the aliphatic amino acid residue; and chymotrypsin cleaves the peptide at the phenylalanine residue. Suitable fluorogenic indicator compounds include xanthine compounds. Preferably, the indicator compounds are rhodamine 110; rhodol; fluorescein; and coumarin, and their derivatives. While, for convenience, the invention is described below with respect to fluorescent leaving groups, it will be appreciated that the leaving groups may alternatively be enzymatic, colorimetric, bioluminescent, chemiluminescent, paramagnetic, luminescent, radioactive, etc.

Each "leaving group" of the compound is a chemical moiety selected so that it will be cleaved by the enzyme to be analyzed. For such embodiment, compounds having a molecular weight of less than about 5,000 are preferred. The leaving group is selected according to the enzyme that is to be assayed. The leaving group will preferably have utility for assaying any of a variety of cellular enzymes, including proteases, caspases, glycosidases, glucosidases, carbohydrases, phosphodiesterases, phosphatases, sulfatases, thioesterases, pyrophosphatases, lipases, esterases, nucleotidases and nucleosidases, as listed above.

The leaving group is preferably selected from amino acids, peptides, saccharides, sulfates, phosphates, esters, phosphate esters, nucleotides, polynucleotides, nucleic acids, pyrimidines, purines, nucleosides, lipids and mixtures thereof. For example, a peptide and a lipid leaving group can be separately attached to a single assay compound such as rhodamine 110. Other leaving groups suitable for the enzyme to be assayed can be determined empirically or obtained from the literature. See, for example, Mentlein, R. et al., H. R., "Influence of Pregnancy on Dipeptidyl Peptidase IV Activity (CD26 Leukocyte Differentiation Antigen) of Circulating Lymphocytes", *Eur. J. Clin. Chem. Clin. Biochem.*, 29, 477–480 (1991); Schon, E. et al., *Eur. J. Immunol.*, 17, 1821–1826 (1987); Ferrer-Lopez, P. et al., "Heparin Inhibits Neutrophil-Induced Platelet Activation Via Cathepsin", *J. Lab Clin. Med.* 119(3), 231–239 (1992); and Royer, G. et al., "Immobilized Derivatives of Leucine Aminopeptidase and Aminopeptidase M.", *J. Biol. Chem.* 248(5), 1807–1812 (1973). These references are hereby incorporated by reference in their entirety.

Examples of such regents include (Cbz-Phe-Arg-NH)$_2$-rhodamine and (Cbz-Pro-Arg-NH)$_2$-rhodamine, which have particularly use in assays for human plasmin and human thrombin, respectively (Leytus, S. P. et al., "New class of sensitive and selective fluorogenic substrates for serine proteases," Biochem. J. 215:253–260 (1983)).

Derivatives of the tetrapeptides ala-ala-pro-leu and ala-ala-pro-val (Beckman Coulter) are preferred assay compounds for assaying the activity of the closely related enzymes leukocyte elastase and pancreatic elastase (leukocyte elastase is also known as neutrophil elastase, EC 3.4.21.37; pancreatic elastase is also known as EC 3.4.21.36) (Stein, R. L. et al. 1987, "Catalysis by human leukocyte elastase: Mechanistic insights into specificity requirements," Biochem. 26:1301–1305; Stein, R. L. et al. 1987, "Catalysis by human leukocyte elastase: Proton inventory as a mechanistic probe," Biochem. 26:1305–1314). Elastases are defined by their ability to cleave elastin, the matrix protein that gives tissues the property of elasticity. Human leukocyte elastase is a serine protease that is a major component of neutrophil granules and is essential for defense against infection by invading microorganisms (Bode, W. et al. 1989, "Human leukocyte and porcine pancreatic elastase: X-ray crystal structures, mechanism, substrate specificity and mechanism-based inhibitors," Biochem. 28:1951–1963)

Aspartic acid-Rho110 (Beckman Coulter) is a preferred assay compound for assaying the activity of the Ca-dependent enzyme aminopeptidase A (aspartate aminopeptidase, angiotensinase A, EC 3.4.11.7). Aminopeptidase A is found in both soluble and membrane-bound forms. Aminopeptidase A is known to cleave the N-terminal aspartic acid amino acid of angiotensin I or II (Jackson, E. K. et al., 1995, "Renin and Angiotensin" in Goodman and Gilman's The Pharmacological Basis of Therapeutics, Ninth Edition McGraw-Hill, NY). Aminopeptidase A is also identical to BP-1/6C3 (Wu, Q. et al., 1991. "Aminopeptidase A activity of the murine B-lymphocyte differentiation antigen BP-1/6C3," Proc. Natl. Acad. Sci, USA. 88: 676–680), a molecule found on early lineage B cells but not on mature lymphocytes. BP-1/6C3 may have a role in the ability to support long-term growth of B cells (Whitlock, C. A., et al., 1987. "Bone marrow stromal cell lines with lymphopoietic activity express high levels of a pre-B neoplasia-associated molecule," Cell 48: 1009–1021.

The conversion of non-fluorescent dichlorofluorescein diacetate (DCFH-DA) (Beckman Coulter) to the highly fluorescent compound 2',7'-dichlorofluorescein (DCF) is a preferred assay compound for monitoring the oxidative burst in polymorphonuclear leukocytes and for determining the presence of peroxides formed through such oxidative bursts (Bass, D. A. et al. "Flow cytometric studies of oxidative product formation by neutrophils: a graded response to membrane stimulation." J. Immunol. 130: 1910–1917). The enzymes responsible for the oxidative burst are rapidly activated in stimulated neutrophils (Weiss, S. J. 1989, "Tissue destruction by neutrophils," N. Eng. J. Med. 320: 365–376). DCFH,PMA Oxidative Burst contains the compound phorbol myristate acetate (PMA), an analogue of the cellular signaling molecule diacylglycerol (DAG) (Alberts, B. et al., Molecular Biology of the Cell, 2nd Edition. Garland Publishing, Inc. New York, pg 704). Therefore, the presence of PMA stimulates processes mediated by DAG, including the oxidative burst. Additionally, resting cells do not have free peroxides and the production of peroxides is rapidly activated by many cell stimuli including the presence of the bacteria or other foreign organisms (Weiss. S. J. 1989, "Tissue destruction by neutrophils," N. Eng. J. Med. 320: 365–376). The production of peroxides due to the oxidative burst can by artificially stimulated by the addition of the compound phorbol myristate acetate (PMA) to the neutrophils (CellProbe substrate DCFH,PMA•Oxidative Burst). DCFH•Peroxides can be used to investigate the effect of other compounds on the oxidative burst including the chemotactic peptide f-met-leu-phe and the yeast product zymosan.

Fluorescein diacetate (FDA) (Beckman Coulter) is a preferred assay compound for assaying the activity of many different non-specific esterases in human tissues (Coates, P. M. et al., 1975, "A preliminary genetic interpretation of the esterase isozymes of human tissues," Ann. Hum. Genet. Lond. 39: 1–20). Acetate esterase activity measured with Napthyl acetate has been used together with other esterase activities to identify leukocyte cell types and is generally high in normal monocytes and megakaryocytes and in blast cells of acute myelomonocytic leukemia, acute monocytic leukemia and acute erythroleukemia. Nelson, D. A. et al., 1990, "Leukocyte esterases in Hematology," 4th Edition, Williams, Beutler, Erslev and Lichtman, Eds. McGraw-Hill.

Fluorescein di-galactopyranoside (Beckman Coulter) is a preferred assay compound for assaying the activity of the galactosidase enzymes (β-galactosidase is also known as lactase, β-D-galactoside galactohydrolase, EC 3.2.1.23; α-galactosidase is also known as melibiase, α-D-galactoside galactohydrolase, EC 3.2.1.22) (Jongkind, J. F. et al., 1986, "Detection of acid-b -galactosidase activity in viable human fibroblasts by flow cytometry," Cytometry 7:463–466). Galactosidase enzymes are lysosomal enzymes that cleave terminal sugar residues from several physiological substrates, including glycoproteins. Gal•galactosidase contains forms of the substrate that are hydrolyzed by both b-galactosidase and a-galactosidase. Impaired galactosidase activity leads to accumulation of partially digested glycoproteins in the lysosomes (Cotran, R. S. et al., 1994, Robbins Pathologic Basis of Disease, 5th Edition. W. B. Saunders Co. pages 138–140). The lysosomes become enlarged, and disrupt normal cell function. The impaired galactosidase activity may be due to mutations in the galactosidase genes or in the processing and transport mechanisms of galactosidase to the lysosomes.

Glycine-phenylalanine-glycine-alanine-Rho110 (Beckman Coulter) is a preferred assay compound for assaying the activity of the collagenase group of proteolytic enzymes in a screen of several tetrapeptide derivatives. Collagenases are enzymes that digest the collagens: macromolecules that form highly organized structures in connective tissue and extracellular matrix. Collagenases and other members of the matrix metalloproteinase family contribute to physiological processes such as postpartum involution of the uterus, wound healing, joint destruction in arthritis, tumor invasion and periodontitis. The collagenases are Zn+2 dependent metallo-enzymes that are synthesized in a proenzyme inactive form (Woessner, J F Jr. 1991. Matrix metalloproteinases and their inhibitors in connective tissue remodeling. FASEB J. 5: 2145–21541). The production of HOCl during the neutrophil oxidative burst has been postulated as one mechanism for collagenase activation in vivo.

The assay compound, fluorescein di-glucuronide (Beckman Coulter) is hydrolyzed by the lysosomal enzyme b-glucuronidase (β-glucuronidase is also known as β-D-glucuroniside glucuronosohydrolase, EC 3.2.1.31). A derivative of β-glucuronide has been used to measure degranulation in polymorphonuclear lymphocytes (PMNs) in a test of the ability of different non-steroidal anti-inflammatory drugs (NSAIDS) to inhibit PMN functions (Kankaanranta, H. et al., 1994, "Effects of non-steroidal anti-inflammatory drugs on polymorphonuclear leukocyte functions in vitro: focus on fenamates," Naunyn-Schmiedeberg's Arch Pharmacol. 350:685–691). Peripheral blood T-lymphocytes display higher β-glucuronidase activity that peripheral blood B-lymphocytes (Crockard, A. et al., 1982, "Cytochemistry of acid hydrolases in chronic B- and T-cell leukemias," Am. J. Clin. Pathol. 78:437–444). Fluorescein di-glucuronide is a negatively charged compound. To help other derivatives of sugars pass through cell membranes in assays of β-glucosidase, a lysomotropic detergent (N-dodecylimidazole) was used (Kohen, E. et al., 1993, "An in situ study of beta-glucosidase activity in normal and gaucher fibroblasts with fluorogenic probes," Cell Biochem. and Function. 11:167–177).

Glycine-proline-Rho110 (Beckman Coulter) is a preferred assay compound for assaying the activity of the serine protease dipeptidyl peptidase IV (DPP IV; Xaa-Pro-dipeptidyl-aminopeptidase, Gly-pro naphthylamidase, EC 3.4.14.5). The membrane bound form of DPP IV is also known as the T-cell activation cell surface marker CD26 (Fleischer, B., 1994, "CD26: a surface protease involved in T-cell activation," Immunol. Today. 15: 180–184). The proteolytic activity of DPP IV may play an essential role in the signaling function of CD26 (Hegen, M. et al., 1993, "Enzymatic activity of CD26 (dipeptidylpeptidase IV) is not required for its signalling function in T cells," Immunobiology. 189: 483–493; Tanaka, T. et al., 1993, "The costimulatory activity of the CD26 antigen requires dipeptidyl peptidase IV enzymatic activity," Proc. Natl. Acad. Sci. USA. 90: 4586–4590). DPP IV cleaves the N-terminal dipeptide from oligopeptides with sequences analogous to the N-terminal sequence of signaling molecules IL-1b, IL-2 and TNF-b, but does not have activity against intact recombinant molecules (Hoffmann, T. et al. 1993, "Dipeptidyl peptidase IV (CD 26) and aminopeptidase N (CD 13) catalyzed hydrolysis of cytokines and peptides with N-terminal cytokine sequences," FEBS Letters. 336: 61–64). Studies of dipeptidyl peptidase IV activity with GP•DPP IV suggest that DPP IV is upregulated in mature thymocytes and among thymocytes which are undergoing programmed cell death (apoptosis) (Ruiz, P. et al., 1996, "Cytofluorographic evidence thatthymocyte dipeptidyl peptidase IV (CD26) activity is altered with stage of ontogeny and apoptotic status," Cytometry. 23: 322–329.

Glycine-proline-leucine-glycine-proline-Rho110 (Beckman Coulter) is a preferred assay compound for assaying the activity of the collagenase group of proteolytic enzymes. Collagenases are Zn+2 dependent metalloenzymes that are synthesized in a pro-enzyme inactive form 1. (Collagenases digest the collagens: macromolecules that form highly organized structures in connective tissue and extracellular matrix. Collagenases and other members of the matrix metalloproteinase family contribute to physiological processes such as postpartum involution of the uterus, wound healing, joint destruction in arthritis, tumor invasion and periodontitis (Woessner, J. F. Jr., 1991, "Matrix metalloproteinases and their inhibitors in connective tissue remodeling," FASEB J. 5: 2145–2154). In a detailed study of the mechanism of hydrolysis of fluorescent derivatives of GPLGP, Kojima et al. found that a collagenase-like peptidase cleaved the substrate at the peptide bond between leu and gly (Kojima, K. et al., 1979, "A new and highly sensitive fluorescence assay for collagenase-like peptidase activity," Anal. Biochem. 100: 43–50).

Lys-Rho 110 (Beckman Coulter) is a preferred assay compound for assaying the activity of aminopeptidase B (EC 3.4.11.6). The aminopeptidases are a group of enzymes which hydrolyze peptide bonds near the N-terminus of polypeptides (International Union of Biochemistry and Molecular Biology. Enzyme Nomenclature. 1992. Academic Press, San Diego). Aminopeptidase B has been purified from the cytosolic fraction of human liver and skeletal muscle and shown to act on synthetic lysyl- or arginyl-substrates. Aminopeptidase B is activated by Cl-1 or Br-1 ions and inhibited by chelating agents and bestatin (Sanderink, G. J. et al., 1988, "Human Aminopeptidases: A Review of the Literature," J. Clin. Chem. Clin. Biochem. 26: 795–807).

Fluorescein di-phosphate (Beckman Coulter) is a preferred assay compound for assaying the activity of the enzyme acid phosphatase (Acid phosphatase is also known as EC 3.1.3.2) (Rotman, B. et al., 1963, "Fluorogenic substrates for b-D-galactosidases and phosphatases derived from fluorescein (3,6-dihydroxyfluoran) and its monomethyl ether,". Proc. Nat. Acad. Sci. USA 50:1–6). Assays of acid phosphatase activity have been used together with assays of esterase activity to identify many different cell types. Monocytes, neutrophils and T-lymphocytes have relatively high acid phosphatase activity while B-lymphocytes have relatively low acid phosphatase activity. (Crockard, A. et al., 1982, "Cytochemistry of acid hydrolases in chronic B- and T-cell leukemias," Am. J. Clin. Pathol. 78:437–444; Li, C. Y. et al., 1970, "Acid phosphatase isoenzyme in human leukocytes in normal and pathologic conditions," J. Histochem. Cytochem. 18:473–481). In addition, blast cells of acute promyelocytic leukemia and acute myelomonocytic leukemia have been shown to have relatively high acid phosphatase activity (Nelson, D. A. et al. 1990, "Leukocyte esterases in Hematology Fourth Edition," Williams W J, Beutler E, Erslev A J and Lichtman M A eds. McGraw Hill, New York.

Arginine-Rho 110 (Beckman Coulter) is a preferred assay compound for assaying the activity of aminopeptidase B (arginyl aminopeptidase, EC 3.4.11.6). The aminopeptidases are a group of enzymes which hydrolyze peptide bonds near the N-terminus of polypeptides (International Union of Biochemistry and Molecular Biology. Enzyme Nomenclature. 1992. Academic Press, San Diego). Aminopeptidase B has been purified from the cytosolic fraction of human liver and skeletal muscle and shown to act on synthetic lysyl- or arginyl-substrates. Aminopeptidase B is activated by Cl-1 or Br-1 ions and inhibited by chelating agents and bestatin (Sanderink, G. J. et al., 1988, "Human Aminopeptidases: A Review of the Literature," J. Clin. Chem. Clin. Biochem. 26: 795–807.

Arg-Gly-Glu-Ser-Rho110 (Beckman Coulter) is a preferred assay compound for assaying the activity of the closely related enzymes leukocyte elastase and pancreatic elastase (leukocyte elastase: neutrophil elastase, EC 3.4.21.37 pancreatic elastase: EC 3.4.21.36). Leukocyte elastase is a serine protease that is a major component of neutrophil granules and is essential for phagocytosis and defense against infection by invading microorganisms (Bode, W. et al., 1989, "Human leukocyte and porcine pancreatic elastase: X-ray crystal structures, mechanism, substrate specificity and mechanism-based inhibitors," Biochem. 28: 1951–1963). The tetrapeptide RGES is part of the sequence of fibronectin (Gartner, T. K. et al., 1985, "The tetrapeptide analogue of the alpha chain and decapeptide analogue of the gamma chain of fibrinogen bind to different sites on the platelet fibrinogen receptor," Blood. 66 Suppl 1: 305a), which is cleaved by human leukocyte elastase (McDonald, J. A. et al., 1980, "Degradation of fibronectin by human leukocyte elastase," J. Biol. Chem. 255: 8848–8858).

The assay compound, threonine-proline-Rho110 (Beckman Coulter) was identified as a substrate for cathepsin C (dipeptidyl-peptidase I, EC 3.4.14.1) and cathepsin G (EC 3.4.21.19) by a screen of many different dipeptide derivatives. Cathepsin C (DPPI) is a lysosomal cysteine peptidase that is found in relative abundance in cytotoxic cells (Thiele, D. L. et al., 1990, "Mechanism of L-leucyl-L-leucine methyl ester-mediated killing of cytotoxic lymphocytes: Dependence on a lysosomal thiol protease, dipeptidyl peptidase I, that is enriched in these cells," Proc. Natl. Acad. Sci. USA. 87: 83–87). Cathepsin G is a serine endopeptidase that is a major component of the azurophil granules of polymorphonuclear leukocytes. Cathepsin G activity is high in promonocytic cells, but reduced in mature monocytes (Hohn, P. A. et al., 1989, "Genomic organization and chromosomal localization of the human cathepsin G gene," J. Biol. Chem. 264: 13412–13419.

Other suitable leaving groups are described in Table 1 of U.S. Pat. No. 5,698,411 (Lucas, et al.) and Landrum et al. (U.S. Pat. No. 5,976,822), and include: (Acetyl-α-D-glucopyranosyl) Rho 110; (Adenine)$_2$ Rho 110; (Adenosine Monophosphate)$_2$ Rho 110; (Adenosine) Rho 110; (B-D-Galactopyranoside)$_2$ Rho 110; (B-D-glucuronide)$_2$ Rho 110; (Butyrl-Thiocholine)$_2$; (Cytosine)$_2$ Rho 110; (Guanine)$_2$ Rho 110; (H Gly)$_2$ Rho 110; (H Gly-Arg)$_2$ Rho 110; (H Gly-Gly-Arg)$_2$ Rho 110; (H Gly-Leu)$_2$ Rho 110; (H Gly-Phe-Gly-Ala)$_2$ Rho 110; (H Gly-Pro-Leu-Gly-Pro)$_2$ Rho 110; (H-Gly)₂ -4'chloro-Rho 110; (H-Gly)₂ Rho 110; (H-Gly-Ala-Ala-Ala)₂ Rho 110; (H-Gly-Arg)₂ Rho 110; (H-Gly-Gly-Arg)₂ Rho 110; (H-Gly-Pro)₂ Rho 110; (H-Gly-Pro-Leu-Gly-Pro) Rho 110; (Hippuryl-His-Leu)₂ Rho 110; (H-L Ala-Ala-Ala-Ala)₂ Rho 110; (H-L Ala-Pro)₂ Rho 110; (H-L Leu-Leu-Arg)₂ Rho 110; (H-L Lys-Ala)₂ Rho 110; (H-L Lys-Ala)₂ Rho 110.Sulfo.4TFA; (H-L Lys-Ala-Lys-Ala)₂ Rho 110; (H-L Pro-Arg)₂ Rho 110; (H-L-Ala)₂-4'chloro-Rho 110; (H-L-Ala)₂ -Rho 110; (H-L-Ala-Ala)₂ Rho 110; (H-L-Ala-Ala-Ala)₂ Rho 110; (H-L-Ala-Ala-Pro-Ala)₂ Rho 110; (H-L-Ala-Ala-Tyr)₂ Rho 110; (H-L-Ala-Arg-Arg)₂ Rho 110; (H-L-Ala-Gly)₂ Rho 110; (H-L-Ala-Phe-Lys)₂ Rho 110; (H-L-Ala-Pro)₂ -Rho 110; (H-L-Ala-Pro-Ala)₂ Rho 110; (H-L-Arg)₂ Rho 110; (H-L-Arg-Arg)₂ Rho 110; (H-L-Arg-Gly-Glu-Ser)₂ Rho 110; (H-L-Asp)₂-Rho 110; (H-L-Cys)₂ -Rho 110; (H-L-Gln-Ser)₂ Rho 110; (H-L-Glu)₂ -Rho 110;; (H-L-Glu-Cys-Gly)₂ Rho 110; (H-L-Glu-Gly-Arg)₂ Rho 110; (H-L-Glu-Gly-Phe)₂ Rho 110; (H-L-Glu-Lys-Lys)₂ Rho 110; (H-L-Gly-Arg)₂ -Rho 110; (H-L-Leu)₂ -4'chloro-Rho 110; (H-L-Leu)₂ Rho 110; (H-L-Leu-Gly)₂ Rho 110; (H-L-Leu-Gly-Leu-Gly)₂ Rho 110; (H-L-Leu-Leu-Arg)₂ Rho 110; (H-L-Lys)₂ Rho 110; (H-L-Lys)₂ -Rho 110; (H-L-Lys-Ala)₂ -Rho 110; (H-L-Lys-Ala)₂ Rho 110-Sulfo; (H-L-Lys-Ala-Arg-Val)₂ Rho 110; (H-L-Lys-Ala-Arg-Val-Phe)₂ Rho 110; (H-L-Lys-Ala-Lys-Ala)₂-Rho 110.6TFA; (H-L-Lys-Pro)₂ Rho 110; (H-L-Lys-Pro)₂ -Rho 110; (H-L-Met)₂ Rho 110; (H-L-Phe-Arg)₂ Rho 110; (H-L-Pro)₂ Rho 110; (H-L-Pro)₂ -Rho 110; (H-L-Pro-Arg)₂ Rho 110; (H-L-Pro-Phe-Arg)₂ Rho 110; (H-L-Ser)₂ Rho 110; (H-L-Serine Phosphate)₂ Rho 110; (H-L-Threonine Phosphate)₂ Rho 110; (H-L-Thr-Pro)₂ Rho 110; (H-L-thyroxine)₂ Rho 110; (H-L-Tyrosine Phosphate)₂ Rho 110; (H-L-Val-Leu-Lys)₂ Rho 110; (H-L-Val-Lys-Val-Lys)₂ Rho 110; (H-L-Val-Pro-Arg)₂ Rho 110; (H-L-Val-Ser)₂ Rho 110; (H-Pro-Arg)₂ -Rho 110; (N-Acetyl MET)₂ Rho 110; (N-Acetyl-L-Ala)₂ FL; (Phosphatidyl-choline)₂ Rho 110; (Saturated Hydrocarbon)₂ Rho 110; (Thymidine)₂ Rho 110; (Triacetin)₂ Rho 110; (Unsaturated Hydrocarton)₂ Rho 110; (Z-Ala-Ala)₂ Rho 110; (Z-Ala-Gly)₂ Rho 110; (Z-Thr-Pro)₂ Rho 110; (γ-Glu)₂ Rho 110; FL(Acetyl-Choline)₂; FL(butyrate)₂; FL(chloroacetate)₂; FL(chlorobutyrate)₂; FL(choline)₂; FL(heptanoate)₂; FL(hexanoate)₂; FL(palmitate)₂; FL(phosphate)₂; FL(propionate)₂; FL(valerate)₂; Fluorescein (acetate)₂; H-L-Leu Rhodol; H-L-Leu Rhodol; Rho 110 (phosphate)₂; Rho 110 (Phosphatidyl-choline)₂; Rho 110 (Phosphatidylinositol)₂; and Rho 110(AMP)₂.

When the leaving group of the assay compound is a salt complex, it will significantly improve the transmission of the assay compound into the cell (Lucas, et al. (U.S. Pat. No. 5,698,411) and Landrum et al. (U.S. Pat. 5,976,822)). The selection of an appropriate salt complex requires a consideration of the compatibility with the cell, solubility in the aqueous media, and cleavage by the enzyme. Care is required in the selection of the peptide salt since isoenzymes have been found to be specific in their recognition of particular salts.

Leaving groups for saccharidases are preferably prepared by the synthesis of monosaccharides, oligosaccharides or polysaccharides comprising between one and about ten sugar residues of the D-configuration. Examples of useful sugars are monosaccharides-pentoses; ribose; deoxyribose; hexose: glucose, dextrose, galactose; oligosaccharides-sucrose, lactose, maltose and polysaccharides like glycogen and starch. The sugar can be an alpha or beta configuration containing from 3 to 7 and preferably 5 to 6 carbon atoms. Analogs of these sugars can also be suitable for the invention. Preferably, the D-configuration of the monosaccharide or disaccharide is utilized. The monosaccharide or disaccharide can be natural or synthetic in origin.

Leaving groups for nucleases, nucleotidases, and nucleosidases are preferably prepared by the synthesis of nucleic acids, purines, pyrimidines, pentose sugars (i.e., ribose and deoxyribose) and phosphate ester. Examples are adenine, guanine, cytosine, uracil and thymine. Leaving groups for restriction enzymes would include polynucleotides. The nucleic acids contain a purine or pyrimidine attached to a pentose sugar at the 1-carbon to N-9 purine or N-1 pyrimidine. A phosphate ester is attached to the pentose sugar at the 5' position. Analogs of these building blocks can also be used.

Leaving groups for lipases are preferably prepared by the synthesis of simple lipids, compound lipids or derived lipids. Simple lipids can be esters of fatty acids, triglycerides, cholesterol esters and vitamin A and D esters. Compound lipids can be phospholipids, glycolipids (cerebrosides), sulfolipids, lipoproteins and lipopolysaccharides. Derived lipids can be saturated and unsaturated fatty acids and mono or diglycerides. Analogs of these lipids can also be used. Examples of lipids are: triglycerides—triolein, fatty acids—linoleic, linolenic and arachidonic; sterols—testosterone, progesterone, cholesterol; phospholipids—phosphatidic acid, lecithin, cephalin (phosphatidyl ethanolamine) sphingomyleins; glycolipids—cerebosides, gangliosides.

Leaving groups for esterases are preferably prepared by the synthesis of carboxylic acids comprising between 2 and 30 carbon atoms. The carboxylic acids can be saturated or unsaturated. The carboxylic acid preferably contains 2 to 24 carbons and more preferably 4 to 24 carbon atoms. Analogs of theses carboxylic acids can also be used. The carboxylic acids can be natural or synthetic in origin. Examples are butyric, caproic, palmitic, stearic, oleic, linoleic and linolenic.

Leaving groups for phosphatases are preferably prepared by the synthesis of phosphates, phosphatidic acids, phospholipids and phosphoproteins. Analogs of these compounds can also be used. Examples are ATP, ADP, AMP and cyclic AMP (c-AMP).

Leaving groups for peptidases are preferably prepared by the synthesis of peptides comprising between one and about ten amino acid residues of the L-configuration. Typically, it has been found that the synthesis of peptides having more than about six amino acids produces a low yield. However, where the yield is acceptable, peptides of greater length can be employed. The amino acids preferably contain 2–10 and preferably 2–8 carbon atoms. Analogs of these amino acids can also be suitable for the invention. If the amino acids are chiral compounds, then they can be present in the D- or L-form or also as a racemate. Preferably, the L-configuration of the amino acid is utilized. The amino acids of the oligopeptide can be natural and/or of synthetic origin. Amino acids of natural origin, such as occur in proteins and peptide antibiotics, are preferred. Synthetic amino acids can also be used, such as pipecolic acid, cyclohexylalanine, phenylglycine, .alpha.-aminocyclohexylcarboxylic acid, hexahydrotyrosine, norleucine, or ethionine.

Suitable methods for synthesizing, purifying, and preparing such compounds for use in cell-based assays are described in Lucas, et al. (U.S. Pat. No. 5,698,411) and Landrum et al. (U.S. Pat. No. 5,976,822), herein incorporated by reference.

In accordance with the methods of the present invention, the detectable signal is preferably detected with a charge-coupled device (CCD) camera or similar detector capable of detecting and storing images resulting from the detected signal. Suitable CCD cameras are available from Alpha-Innotech (San Leandro, Calif.), Stratagene (La Jolla, Calif.), and BioRad (Richmond, Calif.), and Beckman-Coulter (Fullerton, Calif.). The RavidVue™ (Beckman-Coulter) particle shape and size analyzer may be employed for this purpose.

For the automated handling and processing of multiple samples, the SAGIAN™ Automated Assay Optimization™ System (Beckman-Coulter), or the FLUOstar 97™ or POLARstar™ System (BMG), adapted to detect and store images with a CCD camera may be used. The SAGIAN™ Automated Assay Optimization™ System employs a Biomek® 2000 Laboratory Automation Workstation (Beckman-Coulter) with BioWorks™ 3.1 Software (Beckman-Coulter). Automation of the assay can be accomplished using SAGIAN AAO™ Software (Beckman-Coulter) and a computer with Windows® NT 4.0 SP3 and Excel 97 (Microsoft Corporation). Flurorescence can be quantified using ImaGene 4.0 assay quantitation software (BioDiscovery Inc.). The FLUOstar 97™/POLARstar™ System is a fully automated microplate-based fluorescence reader developed to measure data on a vast array of fluorescence assays. Measuring from above or below the microplate enables both tissue culture and FIA applications. The POLARstar can detect definitive receptor binding results through fluorescence polarization readings with 384-well microplates.

Other software (e.g., LEADseeker, etc.) may alternatively be used to facilitate very rapid analysis of high density formats and permit the ultra-high throughput screening of a range of biological assays (Fowler A., et al., "A multi-modality assay platform for ultra-high throughput screening," Curr. Pharm. Biotechnol. 2000 November;1(3): 265–81).

In the case of a binding assay that is quantified by densitometric analysis of a CCD camera-generated image, the dynamic range of the assay is limited by the dynamic range of the camera. For any single exposure, weak signals that are below the limit of detection of the camera will not be detected, while strong signals that are above the saturation limit of the camera cannot be quantified. Although the exposure time can be lengthened to detect and quantify weaker signals, or shortened to detect and quantify stronger signals, altering the exposure time does not change the overall dynamic range of the assay. It merely shifts the range to either lower or higher values.

In accordance with the methods of the present invention, multiple measurements of a binding assay, from multiple images of the same sample generated using multiple exposure times are made. The dynamic range of the assay is therefore increased, dependent on the weakest signal detected on the longest exposure, and on the strongest signal that is below saturation on the shortest exposure.

Unlike other conventional detection schemes, such as film, radiography or colorimetric spectroscopy, the CCD acquires "frames" of information by detecting the number of fluorescent, chemiluminescent, or other detectable events occurring over a selected period of time. Each frame, or a sequence of frames that have been added or summed to provide an image, can be filtered using pulse height analysis techniques to substantially reduce or eliminate background noise. After the first exposure is acquired (recording the extent of reaction in a first time interval), the resulting image can be stored and a additional exposures made in order to record the extent of reaction in additional time intervals. Each such image provides quantitative information about the relative extent of the assay occurring within the time interval involved. Once such multiple images have been obtained, processing techniques may be employed to determine quantitatively or qualitatively the extent of the generated signal.

In one embodiment, the methods of the present invention can be employed to determine the extent of signal generated across all prior time occurring intervals tested. As such, the assay reports the cumulative generation of signal. This aspect of the present invention permits one to expand the dynamic range of the assay, and facilitates the automated processing of multiple samples that may have widely differing concentrations of analyte.

In a second embodiment, the methods of the present invention can be employed to determine and compare the extent of signal generated in each interval tested, so as to permit a determination of the rate of reaction, and the reaction order.

In one embodiment, the CCD will be an area detector CCD, and will be capable of simultaneously recording all light changes occurring in an area (for example, a microtiter well or plate). In an alternative embodiment, a scanning detector CCD may be used. Such a detector scans areas of the assay (for example, individual wells of a microtiter plate, etc.) and then sums the detected changes (see. e.g., Messler P., et al., "Instrumentation for multiwavelengths excitation imaging," J. Neurosci. Methods 1996 November;69(2): 137–47).

Any of a wide variety of assay formats may be used in accordance with the methods of the present invention. They may be heterogenous or homogeneous, and they may be sequential or simultaneous. They may be competitive or non-competitive. U.S. Pat. Nos. 5,563,036; 5,627,080; 5,633,141; 5,679,525; 5,691,147; 5,698,411; 5,747,352; 5,811,526; 5,851,778 and 5,976,822 illustrate several different assay formats and applications.

Heterogeneous immunoassay techniques typically involve the use of a solid phase material to which the reaction product becomes bound. The reaction product is separated from excess sample, assay reagents and other substances by removing the solid phase from the reaction mixture. One type of solid phase immunoassay that may be used in accordance with the present invention is a sandwich immunoassay. In the sandwich assay, the more analyte present in the sample the greater the amount of label present on the solid phase. This type of assay format is generally preferred, especially for the visualization of low analyte concentrations, because the appearance of label on the solid phase is more readily detected. In the sandwich assay, an anti-analyte antibody (capture reagent) is bound to the insoluble solid phase material, as described by Schuurs et al. U.S. Pat. Nos. 3,791,932 and 4,016,043, and by Pankratz, et al., U.S. Pat. No. 5,876,935. A second anti-analyte antibody is labeled with a detectable agent to form an indicator reagent, e.g., the detectable label can be an enzyme which will react with an enzyme substrate to form a detectable product. If the analyte is present in the test sample, then the two antibodies form an immunocomplex with the analyte (i.e., an antibody/analyte/antibody sandwich), and the amount of indicator reagent associated with the solid phase is directly proportional to the amount of analyte in the test sample. When the enzyme substrate is added, it reacts with the enzyme component of the indicator reagent to signal the presence or amount of analyte associated with the solid phase.

In order to eliminate the bound-free separation step and reduce the time and equipment needed for a chemical binding assay, a homogeneous assay format may be used. In such assays, one component of the binding pair may still be immobilized, however, the presence of the second component of the binding pair is detected without a bound-free separation. Examples of homogeneous, optical methods are the EMIT method of Syva, Inc. (Sunnyvale, Calif.), which operates through detection of fluorescence quenching, the laser nephelometry latex particle agglutination method of Behringwerke (Marburg, Germany), which operates by detecting changes in light scatter, the LPIA latex particle agglutination method of Mitsubishi Chemical Industries, the TDX fluorescence depolarization method of Abbott Laboratories (Abbott Park, Ill.), and the fluorescence energy transfer method of Cis Bio International (Paris, France). Any of such assays may be employed in accordance with the present invention.

The binding assay of the present invention may be configured as a competitive assay. In a competitive assay, the more analyte present in the test sample the lower the amount of label present on the solid phase. In a manner similar to the sandwich assay, the competitive assay can involve an anti-analyte binding agent bound to the insoluble solid phase, however, a labeled analyte, instead of a labeled second antibody of the sandwich assay, is used as the indicator reagent. In the competitive assay, the indicator reagent competes with the test sample analyte to bind the capture reagent on the solid phase. The amount of captured indicator reagent is inversely proportional to the amount of analyte present in the test sample. Smith (U.S. Pat. No. 4,401,764) describes an alternative competitive assay format using a mixed binding complex which can bind analyte or labeled analyte but wherein the analyte and labeled analyte can not simultaneously bind the complex. Clagett (U.S. Pat. No. 4,746,631) describes an immunoassay method using a reaction chamber in which an analyte/ligand/marker conjugate is displaced from the reaction surface in the presence of test sample analyte and in which the displaced analyte/ligand/marker conjugate is immobilized at a second reaction site. The conjugate includes biotin, bovine serum albumin and synthetic peptides as the ligand component of the conjugate, and enzymes, chemiluminescent materials, enzyme inhibitors and radionucleotides as the marker component of the conjugate. Li (U.S. Pat. No. 4,661,444) describes a competitive immunoassay using a conjugate of an anti-idiotype antibody and a second antibody, specific for a detectable label, wherein the detectable response is inversely related to the presence of analyte in the sample. Allen (EP 177,191) describes a binding assay involving a conjugate of a ligand analog and a second reagent, such as fluorescein, wherein the conjugate competes with the analyte (ligand) in binding to a labeled binding partner specific for the ligand, and wherein the resultant labeled conjugate is then separated from the reaction mixture by means of solid phase carrying a binding partner for the second reagent. This binding assay format combines the use of a competitive binding technique and a reverse sandwich assay configuration, i.e., the binding of conjugate to the labeled binding member prior to separating conjugate from the mixture by the binding of the conjugate to the solid phase. The assay result, however, is determined as in a conventional competitive assay wherein the amount of label bound to the solid phase is inversely proportional to the amount of analyte in the test sample. Chieregatt et al. (GB Patent No. 2,084,317) describe a similar assay format using an indirectly labeled binding partner specific for the analyte. Mochida et al. (U.S. Pat. No. 4,185,084) also describe the use of a double-antigen conjugate which competes with an antigen analyte for binding to an immobilized antibody and which is then labeled; this method also results in the detection of label on a solid phase wherein the amount of label is inversely proportional to the amount of analyte in the test sample. Sadeh et al. (U.S. Pat. No. 4,243,749) describe a similar enzyme immunoassay wherein a hapten conjugate competes with analyte for binding to an antibody immobilized upon a solid phase. Any of such variant assays may be used in accordance with the present invention.

In all such assay formats, at least one of the components of the assay reagents will be labeled or otherwise detectable by the evolution or quenching of light. Such component may be the analyte being assayed, or a substrate, co-factor, binding partner, or product of a reaction or activity of such analyte, etc. Radioisotopic-binding assay formats (e.g., a radioimmunoassay, etc.) employ a radioisotope as such label; the signal being detectable by the evolution of light in the presence of a fluorescent or fluorogenic moiety (see, Lucas, et al. (U.S. Pat. No. 5,698,411) and Landrum et al. (U.S. Pat. 5,976,822). Enzymatic-binding assay formats (e.g., an ELISA, etc.) employ an enzyme as a label; the signal being detectable by the evolution of color or light in the presence of a chromogenic or fluorogenic moiety. Other labels, such as paramagnetic labels, materials used as colored particles, latex particles, colloidal metals, such as selenium and gold, and dye particles (see, U.S. Pat. Nos. 4,313,734; 4,373,932, and 5,501,985) may also be employed.

All publications and patents mentioned in this specification are herein incorporated by reference to the same extent as if each individual publication or patent application was specifically and individually indicated to be incorporated by reference. Having now generally described the invention, the same will be more readily understood through reference to the following examples, which are provided by way of illustration, and are not intended to be limiting of the present invention, unless specified.

Having now generally described the invention, the same will be more readily understood through reference to the following examples, which are provided by way of illustration, and are not intended to be limiting of the present invention, unless specified.

EXAMPLE 1

Enhanced Detection Assay of Interleukin-8 (IL-8)

In order to illustrate the principles of preferred embodiments of the present invention, a sandwich immunoassay for interleukin-8 activity was conducted and the fluorescence of anti-IL8 detection antibodies was recorded with a CCD camera. The results obtained are shown in FIGS. 1–3.

Figure 1:
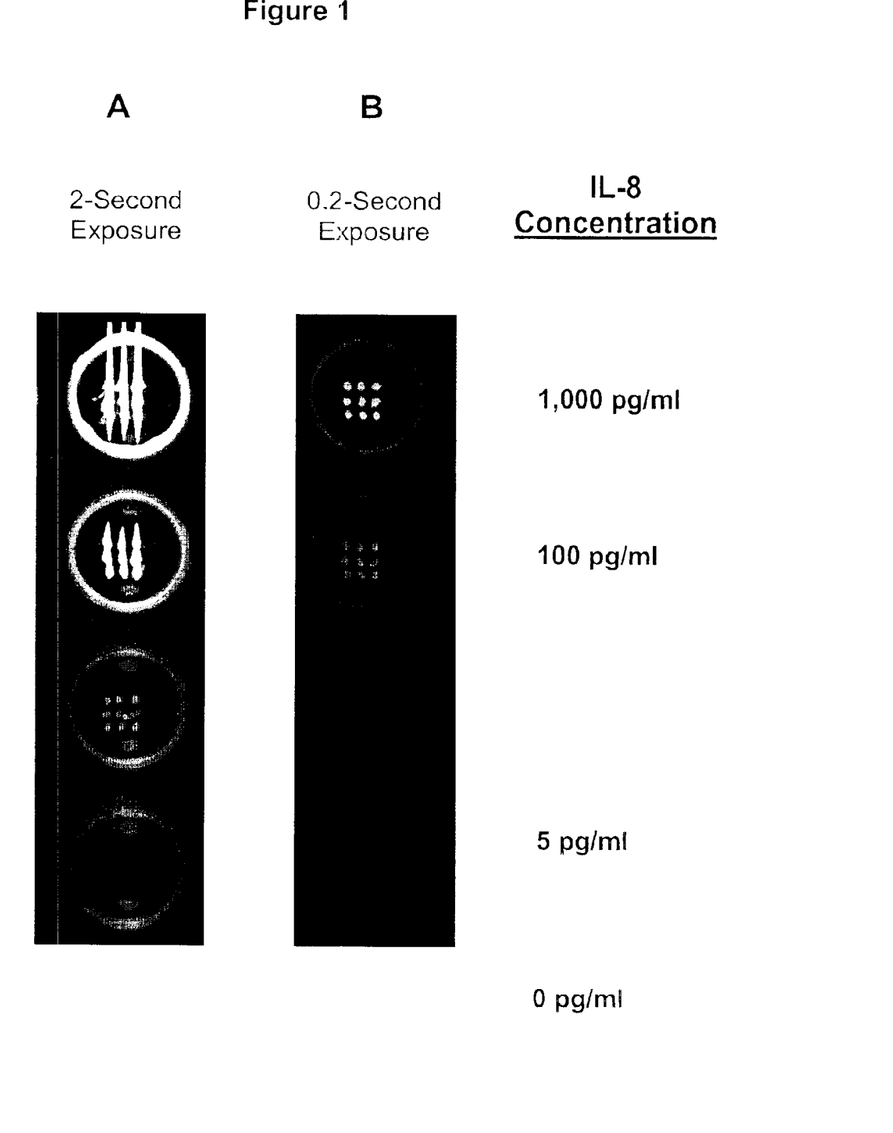
FIG. 1 shows a depiction of a 2-second exposure (A) and a 0.2 second exposure (B), of the fluorescence obtained in a sandwich fluorescence assay for interleukin-8.

Image A in FIG. 1 is a depiction of a 2-second exposure, in which the 5 pg/ml sample is easily detected, but in which the 100 and 1,000 pg/ml samples are off-scale, having saturated the pixels of the CCD camera. Image B in FIG. 1 is a depiction of the result of a shorter (0.2-second) exposure of the same plate. The signal from the 1,000 and 100 pg/ml samples can be easily detected and quantified, but the signal from the 5 pg/ml sample is barely detectable.

Figure 2:
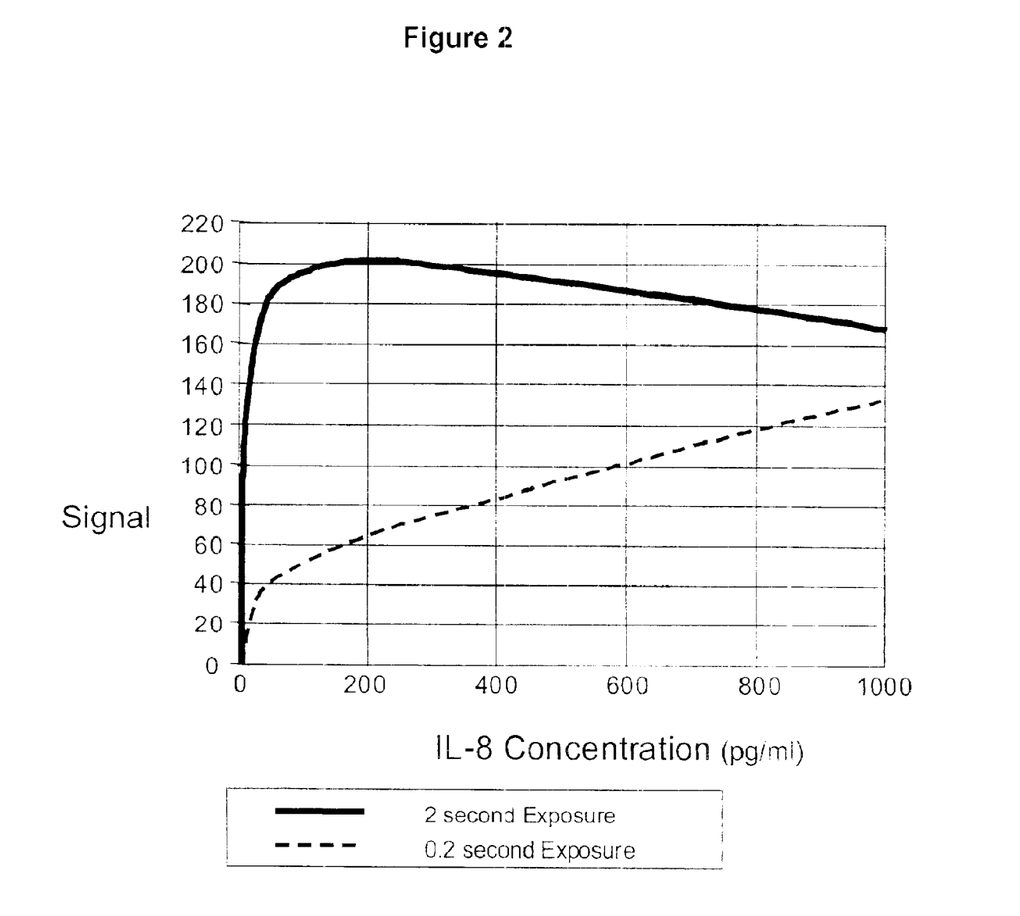
FIG. 2 shows the quantified values for the assay data of FIG. 1 in the range 0–1000 pg/ml.
Figure 3:
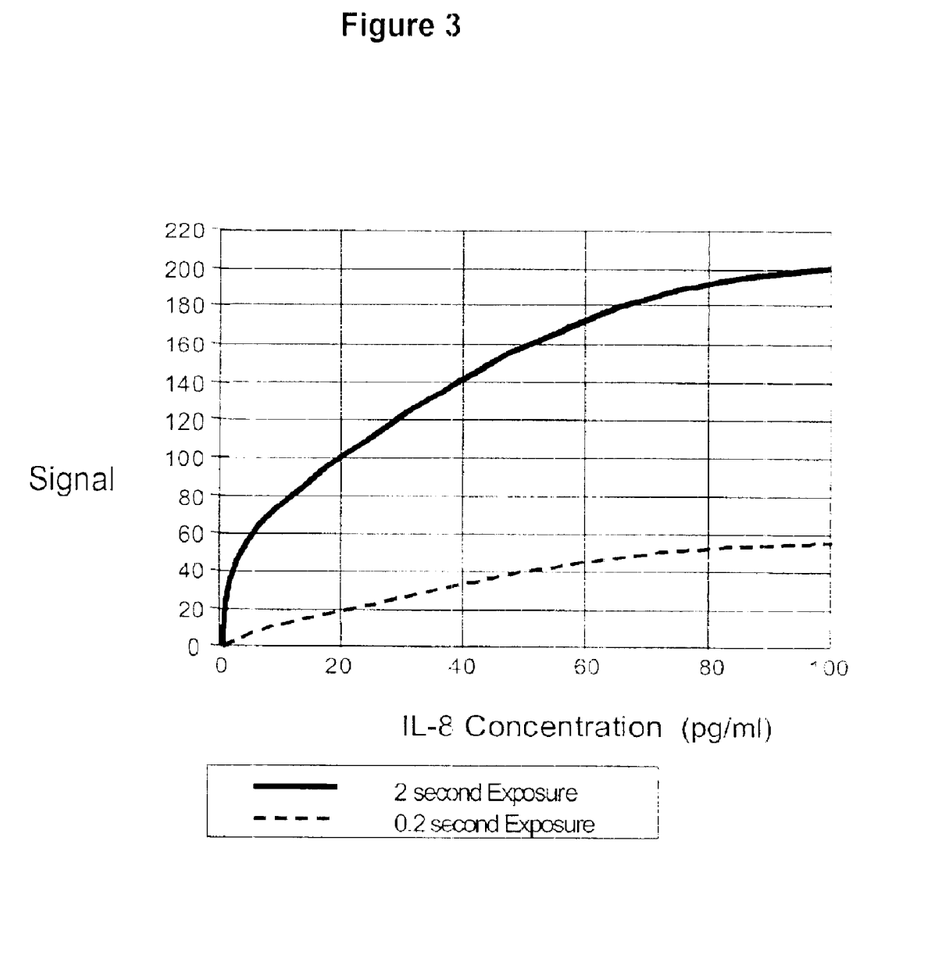
FIG. 3 shows the quantified values for the assay data of FIG. 1 in the range 0–100 pg/ml.

FIGS. 2 and 3 show the quantified values for the assay. Fluorescence was quantified using ImaGene 4.0 assay quantitation software (BioDiscovery Inc.). Each point represents the signal mean from 9 spots; values from the 2-second exposure are shown by a solid line, values from the 0.2- second exposure are shown by a dashed line. The same data is plotted in FIGS. 2 and 3, with differing x-axis scale. FIGS. 2 and 3 show that relatively high IL-8 analyte concentrations (between approximately 100 and 1000 pg/ml) can be reliably quantified from the 0.2 -second exposure (dashed line, FIG. 2), while relatively low analyte concentrations (between approximately 5 to 100 pg/ml) can be reliably quantified from the longer, 2-second exposure (solid line; FIG. 3). Each image from a multiple-exposure assay is analyzed and quantified in a manner identical to a single-exposure assay, so that this method does not add significant complexity to the performance or analysis of the assay. Furthermore, because the analysis of each image is identical, the method is easily automated.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for enhancing the dynamic range of an assay of the presence, absence, activity or concentration of two or more target analytes in one or more samples wherein the presence, absence, activity or concentration of said target analytes is assayed by detecting the emission or quenching of a light signal, wherein said method comprises the steps:
   (A) conducting an assay for the presence, absence, activity or concentration of each of said target analytes in said one or more samples wherein said assays each cause light signals to be emitted or quenched;
   (B) employing a computer system comprising a CCD camera detector to detect said light signals for an initial detection time duration, and to generate data corresponding to said initially detected signals; and
   (C) for each target analyte being assayed, independently causing said computer system to compare said generated data-to data corresponding to the light signal generated by a known concentration of said target analyte and to determine whether said detected signal is within the known dynamic range of said detector's ability to assay that target analyte, wherein, for at least one target analyte said initially detected signal is outside the known dynamic range of said detector's assay for said target analyte, and:
      (1) for each target analyte whose initially detected signal is outside the known dynamic range of said detector's assay for a target analyte, causing said computer system to vary the detection time duration relative to said initial detection time duration until the detected signal for such analyte is within the known dynamic range of said detector's assay for that target analyte, and then causing said computer system to report the presence, absence, activity or concentration of such target analyte; and
      (2) for each target analyte whose initially detected signal is within the known dynamic range of said detector's assay for a target analyte, causing said computer system to report the presence, absence, activity or concentration of such target analyte;
so that, for each target analyte being assayed the presence, absence, activity or concentration of such target analyte is determined using data corresponding to a light signal that is within the dynamic range of said detector's assay for that target analyte.

2. The method of claim 1, wherein said method simultaneously assays the presence, absence, activity or concentration of two or more of said target analytes in said sample.

3. The method of claim 1, wherein said method sequentially assays the presence, absence, activity or concentration of two or more of said target analytes in said sample.

4. The method of claim 1, wherein said step (C) is performed simultaneously for each target analyte being assayed.

5. The method of claim 1, wherein said step (C) is performed sequentially for each target analyte being assayed.

6. The method of claim 1, wherein at least one of said target analyte is selected from the group consisting of an enzyme, a drug or metabolite, a co-factor, a receptor, a receptor ligand, a hormone, a cytokine, a blood factor, a virus, an antigen, a steroid, and an antibody.

7. The method of claim 6, wherein said assay assays the presence, absence, activity or concentration of an enzyme.

8. The method of claim 7, wherein said enzyme is selected from the group consisting of bone specific alkaline phosphatase, aldose reductase, myoglobin, and troponin I.

9. The method of claim 6, wherein said assay assays the presence, absence, activity or concentration of a drug or metabolite.

10. The method of claim 9, wherein said drug or metabolite is selected from the group consisting of: an anti-cancer drug, chemotherapeutic drug, anti-viral drug, non-steroidal anti-inflammatory drug (NSAID), steroidal anti-inflammatory drug, anti-fungal drug, detoxifying drug, analgesic, bronchodilator, anti-bacterial drug, antibiotic drugs, diuretic, digoxin, anti-metabolite, calcium channel blocker, drug for treatment of psoriasis, and a substance of abuse.

11. The method of claim 6, wherein said assay assays the presence, absence, activity or concentration of a co-factor.

12. The method of claim 11, wherein said co-factor is a vitamin, T3, or T4.

13. The method of claim 6, wherein said assay assays the presence, absence, activity or concentration of a cytokine.

14. The method of claim 13, wherein said cytokine is IL-1β, IL-2, IL-3, IL-4, IL-5, IL-6, IL-7, IL-8, IL-10, IL-12, IL-13, TNFα, VEGF, GMCSF, FGFβ, INFγ, EGF, PDGF, MCSF, SCF, insulin, VEGF, Trk, Met, Ron, Axl, Eph, Fas, CD40, CD30, CD27, 4-1BB, LNGFR, OX40, TGFβR, or is a ligand of CCR1, CCR2α, β, CCR3, CCR4, CCR5, CXCR1, CXCR2, CXCR3, CXCR4, BLR1, BLR2, or V28 receptor, or is a ligand of a receptor of IL-2, IL-3, IL-4, IL-5, IL-6, IL-7, IL-8, IL-10, IL-12, or IL-13.

15. The method of claim 6, wherein said assay assays the presence, absence, activity or concentration of a receptor or receptor ligand.

16. The method of claim 15, wherein said receptor or receptor ligand is 4-1BB, Axl, BLR1, BLR2, CCR1, CCR2α, β, CCR3, CCR4, CCR5, CD27, CD30, CD4, CD4, CD40, CXCR1, CXCR2, CXCR3, CXCR4, EGFR, Eph, EPO receptor, Fas receptor, GCSFR, GHR, GMCSFRα, gp130, IFNgRα, IFNgRβ, IFNαR1, insulin-R, IL-1β, IL-2R β, IL-2Rγ chains, IL-4Rα, IL-3Rα, IL-5Rα, IL-6Rα, IL-7Rα, IL-9Rα, IL-10R, IL-11Rα, IL-12Rb1, IL-12Rb2, IL-13Rα, GMCSFRα, IL-3/L-5/GM-CSF receptor common β-chain, LIFR β, LNGFR, MCSFR, Met, OBR, OSMRβ, OX40, PDGFR, PRL, Ron, SCFR, TPOR, TFR, TGFβR, TNFRI, TNFRII, TPOR, Trk, V28, VEGFR.

17. The method of claim 6, wherein said assay assays the presence, absence, activity or concentration of a hormone.

18. The method of claim 12, wherein said hormone is adrenaline, adrenocorticotropic hormone, testosterone, angiotensinogen, antidiuretic hormone, atrial-natriuretic peptide, calcitonin, calcitriol, cholecystokinin, chorionic gonadotropin, cortisol, dopaniine, erythropoietin, estradiol, follicle-stimulating hormone, gastrin, glucagon, gonadotropin-releasing hormone, gorticotropin-releasing hormone, growth hormone, growth hormone-releasing hormone, insulin, insulin-like growth factor-1, leptin, luteinizing hormone, melatonin, aldosterone, neuropeptide Y, noradrenaline, oxytocin, parathyroid hormone, progesterone, prolactin, renin, secretin, somatostatin, theophylline, thiiodothyronine, thrombopoletin, thyroid-stimulating hormone, thyrotropin-releasing hormone, or thyroxine.

19. The method of claim 6, wherein said assay assays a binding activity of an antigen or an antibody.

20. The method of claim 19, wherein said assay assays a binding activity of an antigen characteristic of *Chlamydia, Streptococcus pyogenes* Group A bacteria, *H. pylori,* or *M. tuberculosi,* hepatitis virus, rubella, CMV, HIV, FIV, or prostate specific antigen, or an antibody elicited in response to any of such antigens.

21. The method of claim 6, wherein said assay assays a binding activity of an autoimmune immunoglobulin, thyroglobulin, anti-thyroglobulin, IgE, IgG, or IgM immunoglobulin.

22. The method of claim 6, wherein said assay assays a binding activity of a tumor marker.

23. The method of claim 1, wherein said light signal is an evolution or loss of a fluorescent light signal.

24. The method of claim 1, wherein said light signal is an evolution or loss of a chemiluminescent light signal.

25. The method of claim 1, wherein said light signal is an evolution or loss of an ultraviolet light signal.

26. The method of claim 1, wherein said light signal is an evolution or loss of a visible wavelength light signal.

27. The method of claim 1, wherein said assays are conducted in a multi-well microtiter plate.

28. The method of claim 1, wherein a target analyte has an activity and wherein said computer system additionally calculates the rate of activity of said target analyte in said sample.

* * * * *